(12) United States Patent
Buyda et al.

(10) Patent No.: US 10,987,128 B2
(45) Date of Patent: Apr. 27, 2021

(54) CANNULA ASSEMBLY

(71) Applicant: Covidien LP, Mansfield, MA (US)

(72) Inventors: Oksana Buyda, East Haven, CT (US); Christopher Tokarz, Torrington, CT (US); Amanda Adinolfi, Wallingford, CT (US)

(73) Assignee: COVIDIEN LP, Mansfield, MA (US)

( * ) Notice: Subject to any disclaimer, the term of this patent is extended or adjusted under 35 U.S.C. 154(b) by 132 days.

(21) Appl. No.: 15/919,324

(22) Filed: Mar. 13, 2018

(65) Prior Publication Data

US 2018/0271557 A1 Sep. 27, 2018

Related U.S. Application Data

(60) Provisional application No. 62/568,497, filed on Oct. 5, 2017, provisional application No. 62/516,162, filed (Continued)

(51) Int. Cl.
*A61B 17/34* (2006.01)

(52) U.S. Cl.
CPC ...... *A61B 17/3415* (2013.01); *A61B 17/3421* (2013.01); *A61B 17/3423* (2013.01); (Continued)

(58) Field of Classification Search
CPC ............ A61B 17/3415; A61B 17/3423; A61B 2017/3419; A61B 2017/3445; (Continued)

(56) References Cited

U.S. PATENT DOCUMENTS

| 1,780,912 A | 11/1930 | Gau |
| 1,810,466 A | 6/1931 | Deutsch |

(Continued)

FOREIGN PATENT DOCUMENTS

| DE | 10001695 A1 | 2/2001 |
| DE | 102009014527 A1 | 9/2010 |

(Continued)

OTHER PUBLICATIONS

EP Search Report 11 25 0163 dated Jul. 6, 2011.
(Continued)

*Primary Examiner* — Lauren P Farrar
*Assistant Examiner* — Hamza A Darb
(74) *Attorney, Agent, or Firm* — Carter, DeLuca & Farrell LLP

(57) ABSTRACT

A surgical cannula assembly includes an elongate cannula member having a plurality of longitudinal ribs extending along the longitudinal axis with adjacent longitudinal ribs defining a longitudinal channel therebetween, a fluid port mounted adjacent the proximal end of the cannula member and configured for coupling to a source of inflation fluids, a conduit positioned within at least one longitudinal channel of the cannula member and in fluid communication with the fluid port, and an expandable balloon mounted adjacent the distal end of the cannula member and in fluid communication with the conduit. The expandable balloon is configured to transition from an initial unexpanded condition to an at least partially expanded condition upon passage and entry of inflation fluids from the fluid port, through the conduit and within an internal volume of the expandable balloon.

19 Claims, 16 Drawing Sheets

Related U.S. Application Data on Jun. 7, 2017, provisional application No. 62/474,653, filed on Mar. 22, 2017.

(52) U.S. Cl.
CPC ... *A61B 17/3474* (2013.01); *A61B 2017/3419* (2013.01); *A61B 2017/3445* (2013.01); *A61B 2017/3486* (2013.01); *A61B 2017/3492* (2013.01)

(58) Field of Classification Search
CPC ........ A61B 2017/3486; A61B 17/3474; A61B 2017/3492; A61B 17/3421; A61B 17/0218; A61B 17/00234; A61B 2017/00557; A61B 1/3132; A61B 2017/347; A61B 17/34; A61B 2017/3433; A61B 17/3439; A61B 2017/348; A61B 2017/3482; A61B 2017/3484; A61M 25/1025; A61M 2025/1061; A61M 2025/0233; A61M 13/00; A61M 13/006
See application file for complete search history.

(56) References Cited

U.S. PATENT DOCUMENTS

| | | | |
|---|---|---|---|
| 2,313,164 A | 3/1943 | Nelson |
| 2,541,516 A | 2/1951 | Ivory et al. |
| 2,812,758 A | 11/1957 | Blumenschein |
| 3,782,370 A | 1/1974 | McDonald |
| 3,807,393 A | 4/1974 | McDonald |
| 3,965,890 A | 6/1976 | Gauthier |
| 4,130,113 A | 12/1978 | Graham |
| 4,263,899 A | 4/1981 | Burgin |
| 4,553,537 A | 11/1985 | Rosenberg |
| 5,007,900 A | 4/1991 | Picha et al. |
| 5,052,374 A | 10/1991 | Alvarez-Jacinto |
| 5,080,088 A | 1/1992 | LeVahn |
| 5,125,396 A | 6/1992 | Ray |
| 5,169,387 A | 12/1992 | Kronner |
| 5,231,974 A | 8/1993 | Giglio et al. |
| 5,232,451 A | 8/1993 | Freitas et al. |
| 5,269,754 A | 12/1993 | Rydell |
| 5,279,575 A | 1/1994 | Sugarbaker |
| 5,330,501 A | 7/1994 | Tovey et al. |
| 5,346,484 A | 9/1994 | Van Lindert |
| 5,391,156 A | 2/1995 | Hildwein et al. |
| 5,437,683 A | 8/1995 | Neumann et al. |
| 5,445,615 A | 8/1995 | Yoon |
| 5,460,170 A | 10/1995 | Hammerslag |
| 5,480,410 A | 1/1996 | Cuschieri et al. |
| 5,490,843 A | 2/1996 | Hildwein et al. |
| 5,503,617 A | 4/1996 | Jako |
| 5,520,610 A | 5/1996 | Giglio et al. |
| 5,524,644 A | 6/1996 | Crook |
| 5,556,385 A | 9/1996 | Andersen |
| 5,562,677 A | 10/1996 | Hildwein et al. |
| 5,653,705 A | 8/1997 | de la Torre et al. |
| 5,656,013 A | 8/1997 | Yoon |
| 5,697,891 A | 12/1997 | Hori |
| 5,728,103 A | 3/1998 | Picha et al. |
| 5,755,660 A | 5/1998 | Tyagi |
| 5,755,661 A | 5/1998 | Schwartzman |
| 5,772,583 A | 6/1998 | Wright et al. |
| 5,776,110 A | 7/1998 | Guy et al. |
| 5,779,629 A | 7/1998 | Hohlen |
| 5,788,630 A | 8/1998 | Furnish |
| 5,803,921 A | 9/1998 | Bonadio |
| 5,810,721 A | 9/1998 | Mueller et al. |
| 5,846,193 A | 12/1998 | Wright |
| 5,875,782 A | 3/1999 | Ferrari et al. |
| 5,879,291 A | 3/1999 | Kolata et al. |
| 5,906,577 A | 5/1999 | Beane et al. |
| 5,908,382 A | 6/1999 | Koros et al. |
| 5,931,778 A | 8/1999 | Furnish |
| 5,935,107 A | 8/1999 | Taylor et al. |
| 5,944,736 A | 8/1999 | Taylor et al. |
| 5,951,466 A | 9/1999 | Segermark et al. |
| 5,951,467 A | 9/1999 | Picha et al. |
| 5,957,835 A | 9/1999 | Anderson et al. |
| 5,967,972 A | 10/1999 | Santilli et al. |
| 5,993,385 A | 11/1999 | Johnston et al. |
| 6,024,736 A | 2/2000 | de la Torre et al. |
| 6,033,362 A | 3/2000 | Cohn |
| 6,033,425 A | 3/2000 | Looney et al. |
| 6,036,641 A | 3/2000 | Taylor et al. |
| 6,048,309 A | 4/2000 | Flom et al. |
| 6,074,380 A | 6/2000 | Byrne et al. |
| 6,113,535 A | 9/2000 | Fox et al. |
| 6,120,436 A | 9/2000 | Anderson et al. |
| 6,132,370 A | 10/2000 | Furnish et al. |
| 6,142,935 A | 11/2000 | Flom et al. |
| 6,159,231 A | 12/2000 | Looney et al. |
| 6,162,172 A | 12/2000 | Cosgrove et al. |
| 6,231,506 B1 | 5/2001 | Hu et al. |
| 6,254,533 B1 | 7/2001 | Fadem et al. |
| 6,254,534 B1 | 7/2001 | Butler et al. |
| 6,283,912 B1 | 9/2001 | Hu et al. |
| 6,309,349 B1 | 10/2001 | Bertolero et al. |
| 6,312,377 B1 | 11/2001 | Segermark et al. |
| 6,331,158 B1 | 12/2001 | Hu et al. |
| 6,332,468 B1 | 12/2001 | Benetti |
| 6,354,995 B1 | 3/2002 | Hoftman et al. |
| 6,361,492 B1 | 3/2002 | Santilli |
| 6,382,211 B1 | 5/2002 | Crook |
| 6,432,121 B1 * | 8/2002 | Jervis ............... A61B 17/00234 |
| | | 606/190 |
| 6,443,957 B1 | 9/2002 | Addis |
| 6,450,983 B1 | 9/2002 | Rambo |
| 6,458,079 B1 | 10/2002 | Cohn et al. |
| 6,500,116 B1 | 12/2002 | Knapp |
| 6,517,563 B1 | 2/2003 | Paolitto et al. |
| 6,547,725 B1 | 4/2003 | Paolitto et al. |
| 6,585,442 B2 | 7/2003 | Brei et al. |
| 6,599,240 B2 | 7/2003 | Puchovsky et al. |
| 6,599,292 B1 | 7/2003 | Ray |
| 6,616,605 B2 | 9/2003 | Wright et al. |
| 6,652,454 B2 | 11/2003 | Hu et al. |
| 6,723,044 B2 | 4/2004 | Pulford et al. |
| 6,730,021 B2 | 5/2004 | Vassiliades, Jr. et al. |
| 6,730,022 B2 | 5/2004 | Martin et al. |
| 6,746,396 B1 | 6/2004 | Segermark et al. |
| 6,746,467 B1 | 6/2004 | Taylor et al. |
| 6,814,078 B2 | 11/2004 | Crook |
| 6,814,700 B1 | 11/2004 | Mueller et al. |
| 6,840,951 B2 | 1/2005 | de la Torre et al. |
| 6,846,287 B2 | 1/2005 | Bonadio et al. |
| 6,958,037 B2 | 10/2005 | Ewers et al. |
| 7,033,319 B2 | 4/2006 | Pulford et al. |
| 7,052,454 B2 | 5/2006 | Taylor |
| 7,144,368 B2 | 12/2006 | Larson et al. |
| 7,147,599 B2 | 12/2006 | Phillips et al. |
| 7,179,225 B2 | 2/2007 | Shluzas et al. |
| 7,195,592 B2 | 3/2007 | Ravikumar et al. |
| 7,220,228 B2 | 5/2007 | Hu et al. |
| 7,226,451 B2 | 6/2007 | Shluzas et al. |
| 7,229,408 B2 | 6/2007 | Douglas et al. |
| 7,238,154 B2 | 7/2007 | Ewers et al. |
| 7,261,688 B2 | 8/2007 | Smith et al. |
| 7,270,632 B2 | 9/2007 | Santilli |
| 7,300,399 B2 | 11/2007 | Bonadio et al. |
| 7,344,495 B2 | 3/2008 | Ravikumar et al. |
| 7,387,126 B2 | 6/2008 | Cox et al. |
| 7,393,322 B2 | 7/2008 | Wenchell |
| 7,449,011 B2 * | 11/2008 | Wenchell ........... A61B 17/3421 |
| | | 604/104 |
| 7,473,222 B2 | 1/2009 | Dewey et al. |
| 7,507,202 B2 | 3/2009 | Schoellhorn |
| 7,507,235 B2 | 3/2009 | Keogh et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,566,302 B2 | 7/2009 | Schwer |
| 7,585,277 B2 | 9/2009 | Taylor et al. |

(56) References Cited

U.S. PATENT DOCUMENTS

| | | |
|---|---|---|
| 7,594,888 B2 | 9/2009 | Raymond et al. |
| 7,650,887 B2 | 1/2010 | Nguyen et al. |
| 10,327,809 B2 * | 6/2019 | Buyda ............... A61B 17/3421 |
| 2001/0002429 A1 | 5/2001 | Hu et al. |
| 2001/0020121 A1 | 9/2001 | Hu et al. |
| 2001/0041827 A1 | 11/2001 | Spence et al. |
| 2002/0004628 A1 | 1/2002 | Hu et al. |
| 2002/0095139 A1 | 7/2002 | Keogh et al. |
| 2002/0099269 A1 | 7/2002 | Martin et al. |
| 2002/0099271 A1 | 7/2002 | Knapp |
| 2002/0137989 A1 | 9/2002 | Clem et al. |
| 2003/0191371 A1 | 10/2003 | Smith et al. |
| 2004/0049099 A1 | 3/2004 | Ewers et al. |
| 2004/0054353 A1 | 3/2004 | Taylor |
| 2004/0059192 A1 | 3/2004 | Cartier et al. |
| 2004/0225195 A1 | 11/2004 | Spence et al. |
| 2005/0096508 A1 | 5/2005 | Valentini et al. |
| 2005/0171403 A1 | 8/2005 | Paolitto et al. |
| 2005/0192532 A1 * | 9/2005 | Kucklick ............ A61M 1/0084 |
| | | 604/96.01 |
| 2005/0228232 A1 | 10/2005 | Gillinov et al. |
| 2005/0267336 A1 | 12/2005 | Bertolero et al. |
| 2005/0283050 A1 | 12/2005 | Gundlapalli et al. |
| 2006/0004261 A1 | 1/2006 | Douglas |
| 2006/0089537 A1 | 4/2006 | Schoellhorn |
| 2006/0106416 A1 | 5/2006 | Raymond et al. |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0155170 A1 | 7/2006 | Hanson et al. |
| 2007/0027364 A1 | 2/2007 | Schwer |
| 2007/0073110 A1 | 3/2007 | Larson et al. |
| 2008/0132766 A1 | 6/2008 | Dant et al. |
| 2008/0234550 A1 | 9/2008 | Hawkes et al. |
| 2009/0204067 A1 | 8/2009 | Abu-Halawa |
| 2009/0221960 A1 * | 9/2009 | Albrecht ............ A61B 17/3421 |
| | | 604/103.03 |
| 2009/0265941 A1 | 10/2009 | Kurrus |
| 2009/0299148 A1 | 12/2009 | White et al. |
| 2010/0204707 A1 * | 8/2010 | Tanaka ................. A61M 25/04 |
| | | 606/108 |
| 2010/0210916 A1 | 8/2010 | Hu et al. |
| 2010/0234689 A1 | 9/2010 | Wagner et al. |
| 2015/0073223 A1 * | 3/2015 | Pravongviengkham .................... |
| | | A61B 17/0218 |
| | | 600/207 |
| 2015/0209078 A1 * | 7/2015 | Nevler ............... A61B 17/3417 |
| | | 604/96.01 |
| 2016/0045719 A1 * | 2/2016 | Ha .................... A61M 25/0021 |
| | | 606/196 |

FOREIGN PATENT DOCUMENTS

| | | |
|---|---|---|
| EP | 0177177 A2 | 4/1986 |
| EP | 2179699 A1 | 4/2010 |
| EP | 2228014 A1 | 9/2010 |
| EP | 2228024 A1 | 9/2010 |
| EP | 2238931 A1 | 10/2010 |
| EP | 2335619 A1 | 6/2011 |
| EP | 2417922 A1 | 2/2012 |
| GB | 2275420 A | 8/1994 |
| WO | 9500197 A1 | 1/1995 |
| WO | 9515715 A1 | 6/1995 |
| WO | D108563 A2 | 2/2001 |
| WO | D3034908 A2 | 5/2003 |
| WO | 2005089655 A1 | 9/2005 |
| WO | 2010136805 A1 | 12/2010 |
| WO | 2011079374 A1 | 7/2011 |

OTHER PUBLICATIONS

EP Search Report 11 25 0164 dated Aug. 6, 2011.
EP Search Report 11 25 0719 dated Nov. 16, 2011.
Ep Search Report 11 18 9987 dated Feb. 15, 2012.
EP Search Report 12160423.5 dated Jun. 25, 2012.
European Search Report issued in European Application No. EP18163035.1 dated Oct. 9, 2018.
Partial Euorpean Search Report issued in corresponding European Application No. 18163035.1 dated Jul. 6, 2018.

* cited by examiner

CANNULA ASSEMBLY

CROSS-REFERENCE TO RELATED APPLICATIONS

This application claims the benefit of and priority to U.S. Provisional Patent Application Ser. No. 62/568,497, filed Oct. 5, 2017, and U.S. Provisional Patent Application Ser. No. 62/516,162, filed Jun. 7, 2017, and U.S. Provisional Patent Application Ser. No. 62/474,653, filed Mar. 22, 2017, the entire contents of each of which are incorporated herein by reference.

BACKGROUND

1. Field of the Disclosure

The present disclosure generally relates to a surgical cannula assembly for use in an endoscopic or laparoscopic surgical procedure.

2. Description of the Related Art

Minimally invasive surgical procedures including both endoscopic and laparoscopic procedures permit surgery to be performed on organs, tissues and vessels far removed from an opening within the tissue. In laparoscopic procedures, the abdominal cavity is insufflated with an insufflation gas, e.g., $CO_2$, to create a pneumoperitoneum thereby providing access to the underlying organs. A laparoscopic instrument is introduced through a cannula accessing the abdominal cavity to perform one or more surgical tasks. The cannula may incorporate a seal to establish a substantially fluid tight seal about the instrument to preserve the integrity of the pneumoperitoneum.

While minimally invasive surgical procedures have proven to be quite effective in surgery, several limitations remain. For example, the cannula which is subjected to the pressurized environment, i.e., the pneumoperitoneum, may exhibit a tendency to back out of the incision in the abdominal wall particularly during manipulation of the instrument within the cannula. Conventional cannulas may incorporate an inflatable balloon at the end of the cannula in an effort to resist withdrawal of the cannula from the tissue site. These cannulas typically include a single fluid path or a double tube design to convey inflation fluids such as CO2, saline or air to the inflatable balloon. However, cannulas with a single fluid path may be ineffective in the event the fluid path is clogged or collapses. Double tube designs are complex and difficult to manufacture, and also increase the overall profile of the cannula.

SUMMARY

Accordingly, the present disclosure is directed a surgical cannula assembly which overcomes the disadvantages associated with the prior art. In accordance with one embodiment, the surgical cannula assembly includes an elongate cannula member having a plurality of longitudinal ribs extending along a longitudinal axis thereof with adjacent longitudinal ribs defining a longitudinal channel therebetween, a fluid port configured for coupling to a source of inflation fluids, a conduit positioned within at least one longitudinal channel of the cannula member and in fluid communication with the fluid port, and an expandable balloon mounted adjacent a distal end of the cannula member and in fluid communication with the conduit. The expandable balloon is configured to transition from an initial unexpanded condition to an at least partially expanded condition upon passage and entry of inflation fluids through the conduit and within an internal volume of the expandable balloon.

In embodiments, an outer sleeve is coaxially mounted about the cannula member and coupled to the expandable balloon. In some embodiments, the outer sleeve and the expandable balloon are monolithically formed, e.g., from an elastomeric material.

In other embodiments, a plurality of conduits is provided. Each conduit is positioned within a respective longitudinal channel defined by adjacent longitudinal ribs. Each conduit is in fluid communication with the fluid port and with the internal volume of the expandable balloon.

In embodiments, a cannula housing is mounted adjacent a proximal end of the cannula member. The cannula housing includes an inflation connector in fluid communication with a longitudinal lumen defined within the cannula member.

In another embodiment, a surgical cannula assembly includes a cannula housing and a cannula member defining a longitudinal axis, and a longitudinal lumen configured to permit passage of a surgical object. The cannula member has a plurality of longitudinal ribs on an outer surface thereof with adjacent longitudinal ribs defining longitudinal channels therebetween. A conduit is at least partially positioned within one longitudinal channel of the cannula member. A fluid port is in fluid communication with the conduit and configured for coupling to a source of inflation fluids. An outer sleeve is coaxially mounted about the cannula member. The outer sleeve includes an expandable balloon which is in fluid communication with the conduit. The expandable balloon is configured to transition from an initial unexpanded condition to an at least partially expanded condition upon passage of inflation fluids from the fluid port, through the conduit and within an internal volume of the expandable balloon.

In embodiments, a second conduit is at least partially positioned within a second longitudinal channel of the cannula member and is in fluid communication with the fluid port and with the internal volume of the expandable balloon.

In some embodiments, the cannula member includes a second longitudinal channel defined between adjacent longitudinal ribs. The second longitudinal channel is in fluid communication with the fluid port to convey inflation fluids to the internal volume of the expandable balloon.

In another embodiment, a surgical cannula assembly includes a cannula housing and a cannula member defining a longitudinal axis, and a longitudinal lumen configured to permit passage of a surgical object. The cannula member includes a plurality of longitudinal ribs on an outer surface thereof with adjacent longitudinal ribs defining longitudinal channels therebetween. A fluid port is configured for coupling to a source of inflation fluids and is in fluid communication with the longitudinal channels of the cannula member. An outer sleeve is coaxially mounted about the cannula member and has an expandable balloon in fluid communication with the longitudinal channels of the cannula member. The expandable balloon is configured to transition from an initial unexpanded condition to an at least partially expanded condition upon passage of inflation fluids from the fluid port, through the longitudinal channels and within an internal volume of the expandable balloon.

In another embodiment, a surgical cannula assembly includes a cannula housing and a cannula member defining a longitudinal axis and a longitudinal lumen configured to permit passage of a surgical object. The cannula member has a single longitudinal groove in an outer surface thereof. A conduit is at least partially positioned within the single longitudinal groove of the cannula member. A fluid port is in fluid communication with the conduit and configured for coupling to a source of inflation fluids. An outer sleeve is coaxially mounted about the cannula member. The outer sleeve has an expandable balloon segment in fluid communication with the conduit. The expandable balloon segment is configured to transition from an initial unexpanded condition to an at least partially expanded condition upon passage of inflation fluids from the fluid port, through the conduit and within an internal volume of the expandable balloon segment.

In embodiments, the outer sleeve extends along a majority of a longitudinal length of the cannula member. In some embodiments, the outer sleeve is secured to the cannula member adjacent proximal and distal ends of the balloon segment. In other embodiments, the outer sleeve comprises an elastomeric material. In certain embodiments, the longitudinal groove of the cannula member includes a single conduit therein. In embodiments, the single longitudinal groove of the cannula member is in parallel relation with the longitudinal axis of the cannula member.

The cannula assembly of the present disclosure is highly effective in uniformly expanding the expandable balloon. In embodiments incorporating multiple longitudinal channels of the cannula member, the multiple longitudinal channels with or without conduits ensures inflation of the expandable member even in the event of clogging or collapse of one or more channels and/or conduits. The outer sleeve surrounding the cannula member provides structural stability while enclosing the longitudinal channels and the conduits providing sealed pathways for passage of inflation fluids to the expandable balloon. In embodiments incorporating a single longitudinal groove with a single conduit disposed therein, the single conduit provides predetermined flow rates of insufflation and deflation to respectively expand and deflate the balloon segment in a controlled and uniform manner.

Other features of the present disclosure will be appreciated from the following description.

BRIEF DESCRIPTION OF THE DRAWINGS

Various aspects and features of the present disclosure are described hereinbelow with references to the drawings, wherein.

DETAILED DESCRIPTION

Particular embodiments of the present disclosure are described hereinbelow with reference to the accompanying drawings. However, it is to be understood that the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to employ the present disclosure in virtually any appropriately detailed structure.

In general, the cannula assembly of the present disclosure includes a cannula member with associated structure which facilitates rapid and uniform expansion of an expandable balloon disposed at the distal end of the cannula member. The cannula assembly includes longitudinal ribs which enhance the structured stability of the cannula member while defining multiple longitudinal channels through which inflation fluids may flow to the internal volume of the expandable balloon. The longitudinal channels are radially spaced about the outer surface of the cannula member to provide uniform expansion of the expandable balloon. Conduits may be positioned within the longitudinal channels to deliver inflation fluids to the expandable balloon. The cannula assembly further includes an outer sleeve coaxially mounted about the cannula member. The outer sleeve may be formed of an elastomeric material and encloses and optionally seals the longitudinal channels. In some embodiments, the elastomeric outer sleeve incorporates the expandable balloon, i.e., the expandable balloon is pre-formed as part of the outer sleeve.

Figure 1:
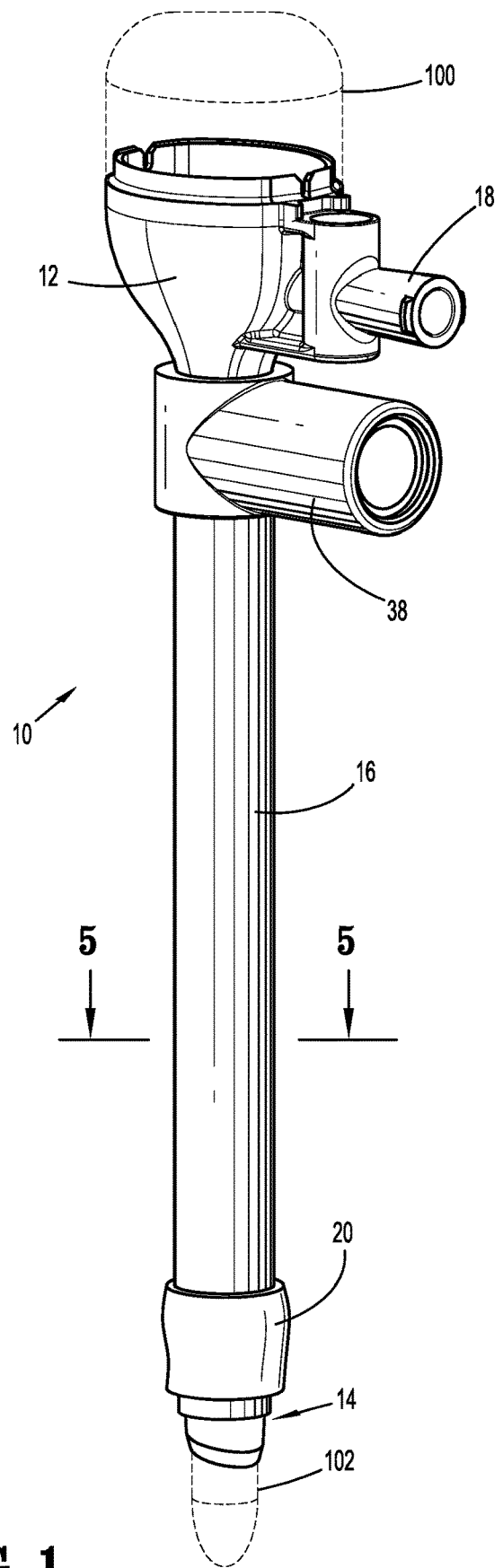
FIG. 1 is a perspective view of the surgical cannula assembly of the present disclosure illustrating the cannula housing, the cannula member extending from the cannula housing, the outer sleeve coaxially positioned about the cannula member and the expandable balloon.

Referring initially to FIG. 1, there is illustrated the surgical cannula assembly of the present disclosure. The cannula assembly 10 is intended to permit access to an insufflated abdominal cavity during a laparoscopic procedure to permit the introduction of a surgical object for performing various surgical tasks on internal organs within the cavity. The surgical object may be a surgical instrument such as laparoscopic or endoscopic clip appliers, graspers, dissectors, retractors, staplers, laser probes, photographic devices, tubes, endoscopes and laparoscopes, electro-surgical devices and the like. Alternatively, the object may be the surgeon's arm or hand, e.g. when used during laparoscopic procedures where the hand is introduced within the abdominal cavity, to directly assist in performing a surgical task. In FIG. 1, the cannula assembly 10 is illustrated with an obturator 100 positioned therein (in phantom) to facilitate access to the abdominal cavity. The obturator 100 may be any conventional obturator 100 having a penetrating tip 102 configured to penetrate tissue.

With continued reference to FIG. 1, the cannula assembly 10 includes a cannula housing 12, a cannula member 14 extending from the cannula housing 12 and an outer sleeve 16 coaxially mounted over the cannula member 14. The cannula housing 12 is dimensioned for engagement by the clinician and may include one or more internal seals (not shown) adapted to establish a seal about a surgical object introduced therethrough. The cannula housing 12 also may include an insufflation connector 18 (e.g., a luer connector) for connecting to a source of insufflation fluids (not shown) for delivery within, e.g., the abdominal cavity. An expandable balloon 20 (shown in an initial unexpanded condition) is coupled to the outer sleeve 16.

Figure 2:
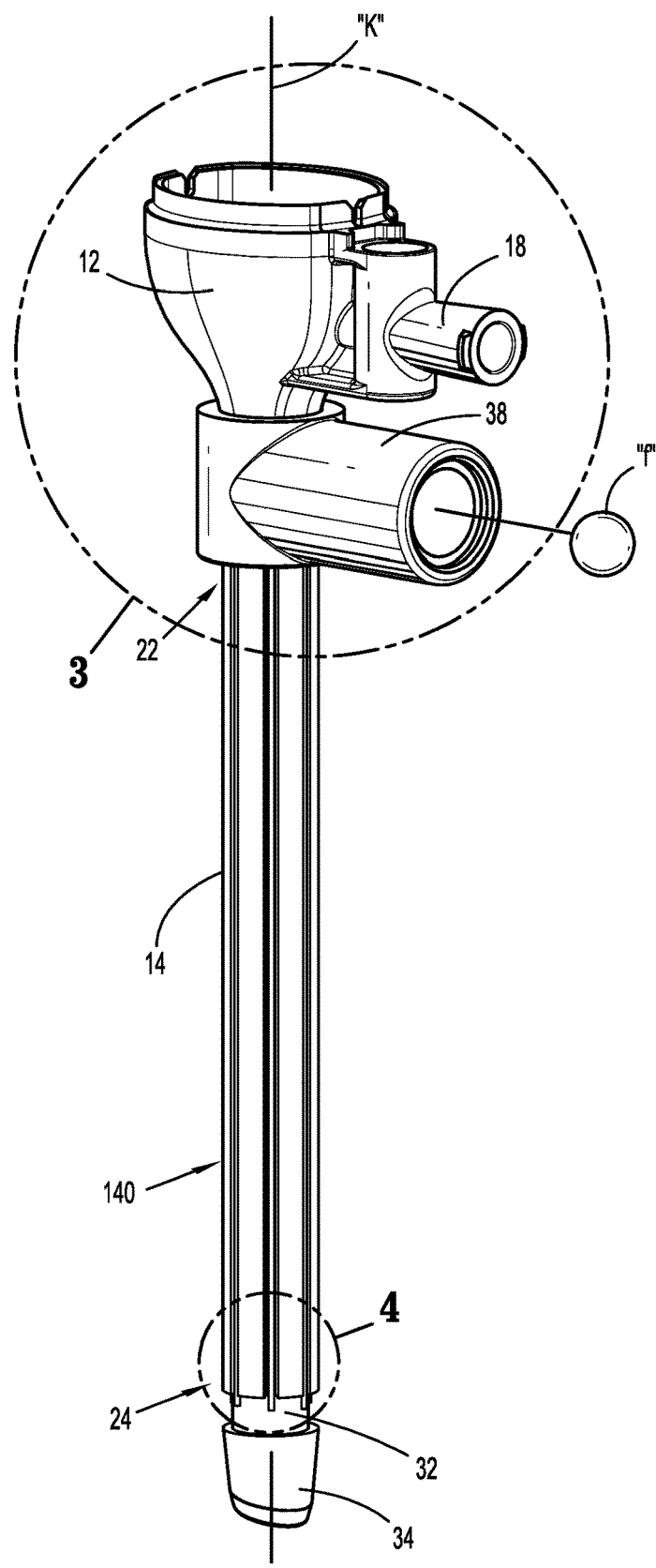
FIG. 2 is a perspective view of the surgical cannula assembly with the outer sleeve and the expandable balloon removed to illustrate the longitudinal ribs of the cannula member.
Figure 3:
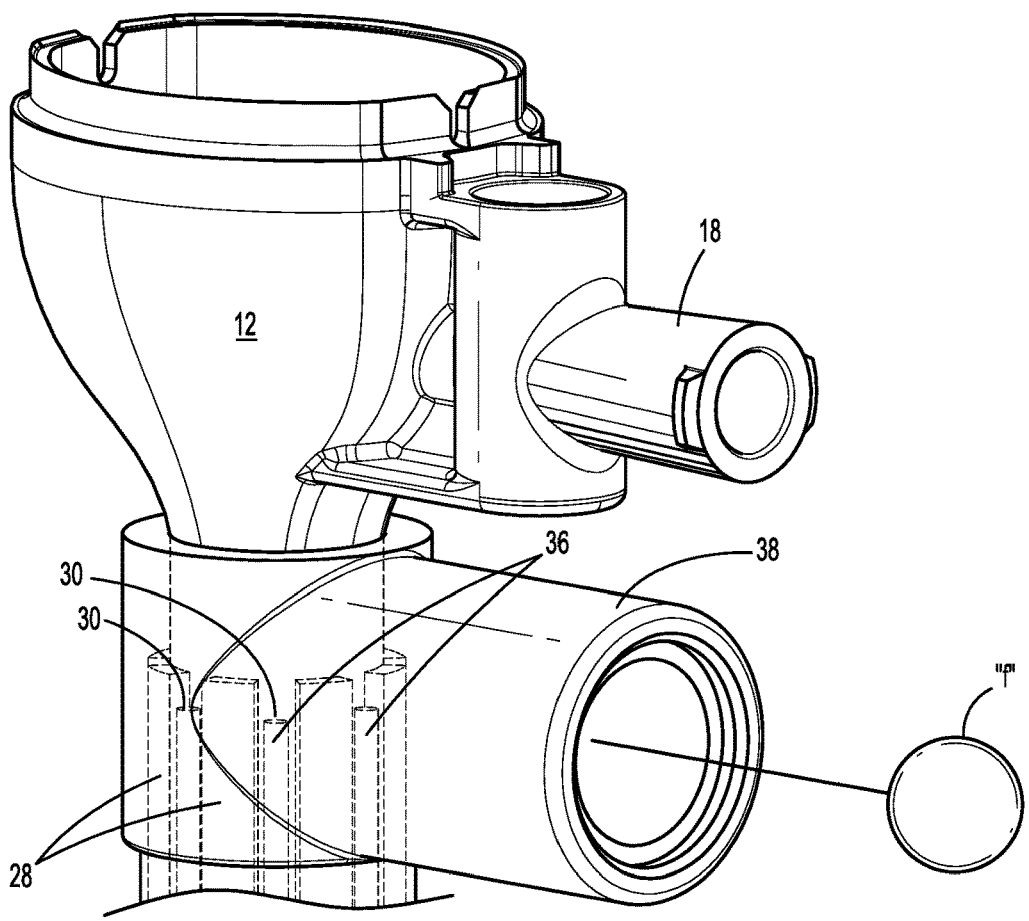
FIG. 3 is an enlarged view of the area of detail depicted in FIG. 2 illustrating the conduits positioned within longitudinal channels defined between adjacent longitudinal ribs.
Figure 4:
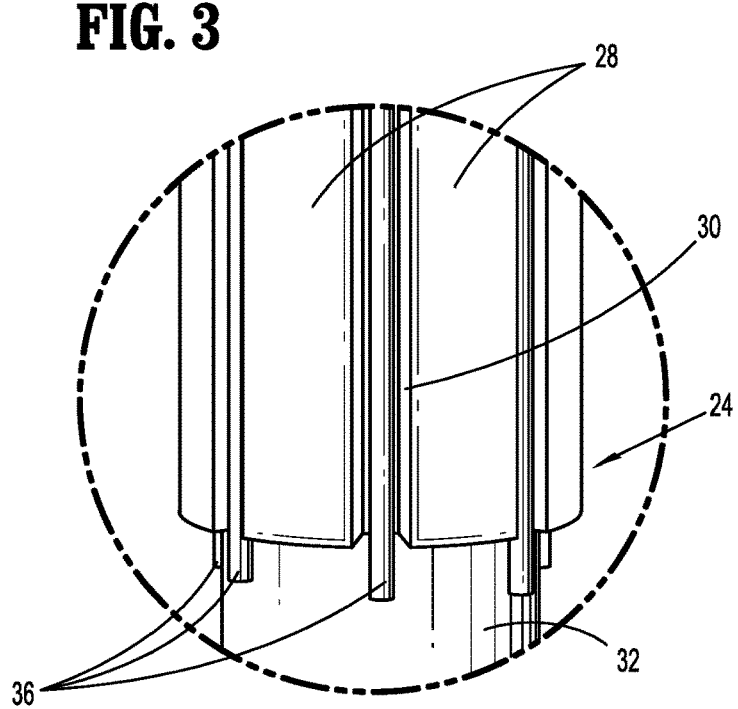
FIG. 4 is an enlarged view of the area of detail depicted in FIG. 2 illustrating the conduits terminating adjacent the distal end of the cannula member.

Referring now to FIGS. 2-4, which depict the outer sleeve 16 and the expandable balloon 20 removed for illustrative purposes, the cannula member 14 has proximal and distal ends 22, 24, and defines a longitudinal axis "k" along which the cannula member 14 extends. The cannula member 14 has an inner surface 14$i$ defining a longitudinal lumen 26 (FIG. 5) to permit passage of the surgical object, and an outer surface 14$o$. The longitudinal lumen 26 is also in fluid communication with the insufflation connector 18 to convey insufflation fluids into the abdominal cavity to establish and/or maintain the pneumoperitoneum.

Figure 5:
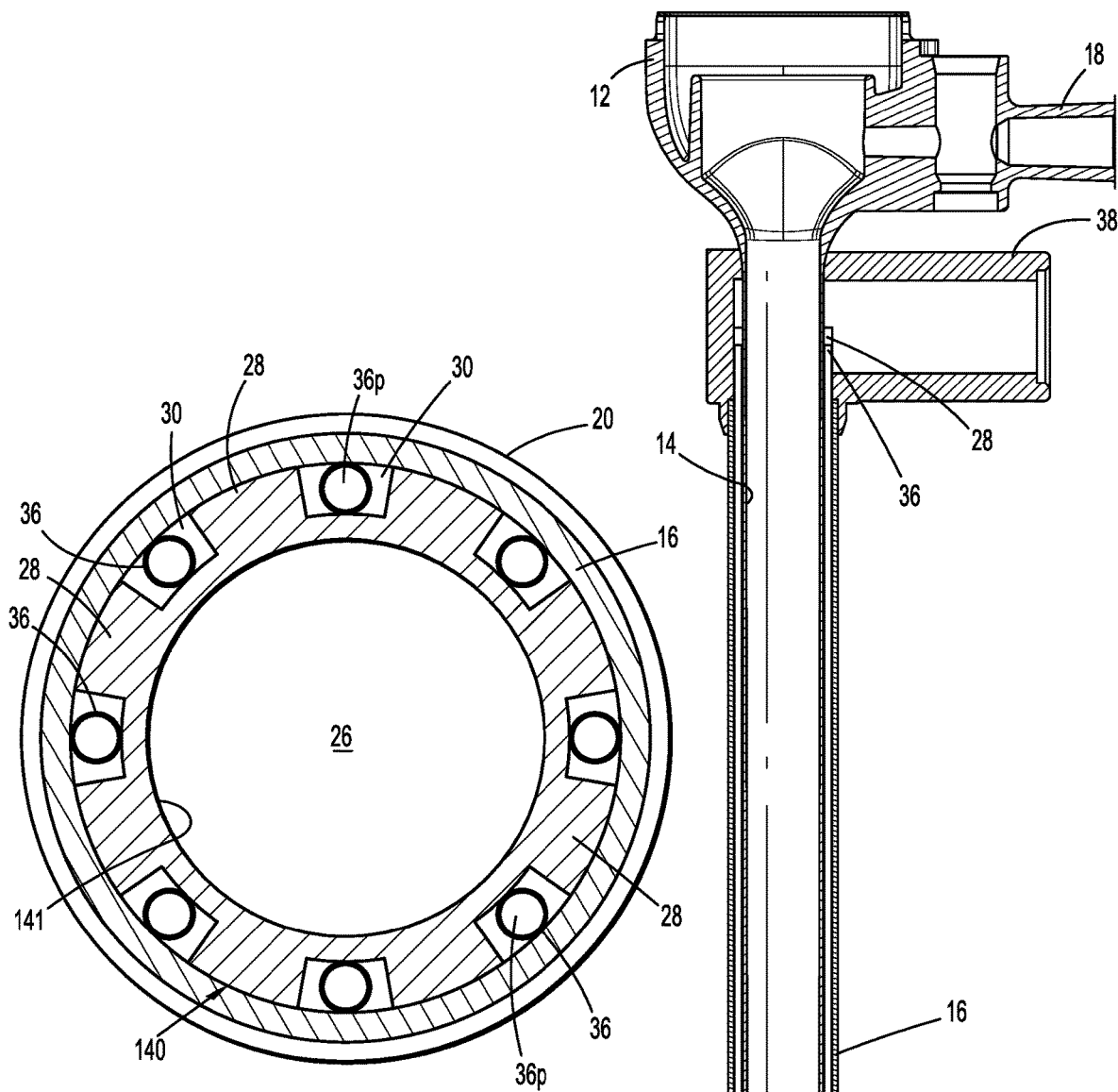
FIG. 5 is a cross-sectional view taken along the lines 5-5 of FIG. 1 further illustrating the longitudinal ribs, the conduits positioned within the longitudinal channels and the outer sleeve.

With reference to the cross-sectional view of FIG. 5, in conjunction with FIGS. 2-4, the cannula member 14 includes a plurality of longitudinal ribs 28 extending along a majority of the length of its outer surface 14$o$. In embodiments, the longitudinal ribs 28 are in parallel relation to the longitudinal axis "k". The longitudinal ribs 28 may be configured to enhance the structural stability of the cannula member 14. Radially adjacent longitudinal ribs 28 define longitudinal channels 30 therebetween which also extend along a majority of the length of the cannula member 14 and in parallel relation to the longitudinal axis "k". In the alternative, the longitudinal ribs 28 and the longitudinal channels 30 may be obliquely arranged relative to the longitudinal axis "k" or may have one or more curvatures. The longitudinal channels 30 may be arranged about the longitudinal axis "k" in equidistant radial spaced relation, or, alternatively, be spaced at different intervals or randomly spaced.

The cannula member 14 further defines an annular recess 32 (FIGS. 2 and 4) adjacent its distal end 24 where the longitudinal ribs 28 and the longitudinal channels 30 terminate. A cannula tip 34 of the cannula member 14 is disposed distal of the annular recess 32, and is configured to facilitate passage through tissue.

A conduit 36 is positioned within at least one longitudinal channel 30 of the cannula member 14. The conduit 36 may be a tube-like structure defining a passage 36$p$ for conveying inflation fluids. In embodiments, a conduit 36 is disposed in more than one longitudinal channel 30, and, in some embodiments, a conduit 36 is positioned within each longitudinal channel 30. The conduits 36 extend into the annular recess 32 of the cannula member 14. As best depicted in FIG. 5, the conduits 36 each define a diameter which is no greater than the depth of a respective longitudinal channel 30. With this arrangement, the conduits 36 do not radially extend beyond the longitudinal ribs 28 or the outer surface 14$o$ of the cannula member 14, thereby reducing the overall profile of the cannula member 14, and minimizing penetration force required to advance the cannula member 14. In the alternative, the conduits 36 may radially extend beyond the outer surface 14$o$ of the cannula member 14. In this embodiment, the conduits 36 may be fabricated from a relatively soft material, e.g., polyurethane, and be compressed to assume an oval shape upon assembly of the outer sleeve 16 over the cannula member 14. Through this compression by the outer sleeve 16, the conduits 36 will not extend beyond the longitudinal ribs 28 or the outer surface of the cannula member 14. In a further alternative, the conduits 36 may be fabricated from a relatively rigid material including a metal or a polymeric material.

Referring again to FIG. 3, the cannula member 14 further includes a fluid port 38 positioned adjacent the cannula housing 12. The fluid port 38 is configured for coupling to a source of inflation fluids "f" via a syringe, tubing or the like. The fluid port 38 surrounds the proximal ends of the conduits 36 and is in fluid communication with the conduits 36 such that inflation fluids introduced within the fluid port 38 are conveyed by the conduits 36 toward the annular recess 32 of the cannula member 14.

Figure 6:
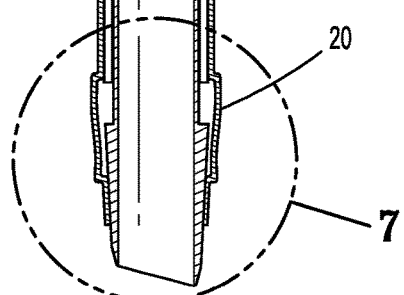
FIG. 6 is a side cross-sectional view of the cannula assembly illustrating the expandable balloon in an unexpanded condition.
Figure 7:
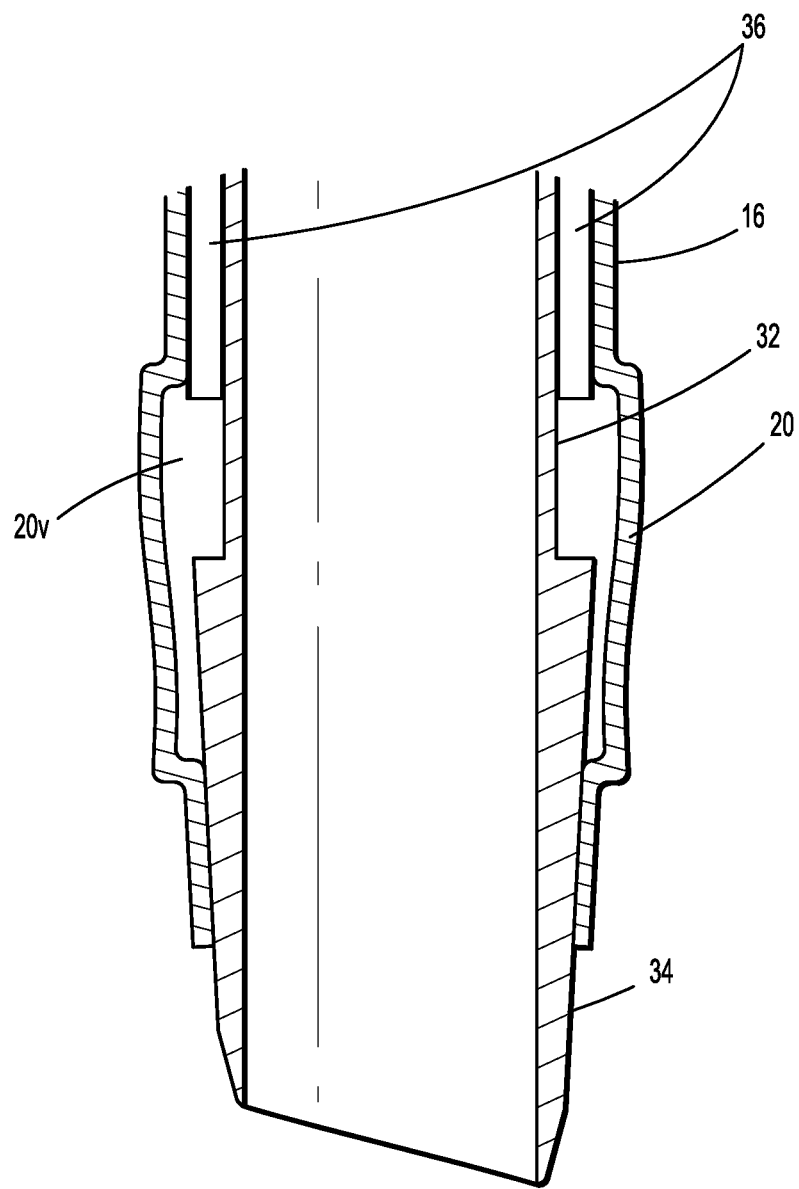
FIG. 7 is an enlarged view of the area of isolation depicted in FIG. 6 illustrating the conduits terminating within the expandable balloon.

Referring now to FIGS. 5-7, the outer sleeve 16 will be discussed. The outer sleeve 16 is coaxially mounted about the cannula member 14 and extends from a position within the fluid port 38 to a position adjacent the distal end 24 of the cannula member 14. The outer sleeve 16 may extend along a majority of the longitudinal length of the cannula member 14. The outer sleeve 16 encloses the conduits 36 within the longitudinal channels 30 thereby providing structural support to the assembled components. The outer sleeve 16 may be secured within the fluid port 38 and to the cannula member 14 through a friction or interference fit or with the use of adhesives, cements, welding or the like. In one embodiment, the outer sleeve 16 is fabricated from an elastomeric material such as silicone rubber, polyurethane, polyester or the like. In this embodiment, the outer sleeve 16 may define a diameter approximating the diameter of the cannula member 14 to enclose the longitudinal channels 30 and the conduits 36 in frictional sealing relation therewith. Alternatively, the outer sleeve 16 may have a diameter less than the diameter of the cannula member 14, and is stretched to be positioned about the cannula member 14. Once positioned on the cannula member 14, the outer sleeve 16 is fixed from longitudinal movement, and serves as, e.g., an enclosure enclosing, and optionally sealing, the cannula member 14, longitudinal ribs 28 and the longitudinal channels 30. In embodiments, the outer sleeve 16 is secured within, about or relative to the fluid port 38 in sealed relation therewith.

The expandable balloon 20 is coupled to the outer sleeve 16 and is coaxially mounted about the distal end 24 of the cannula member 14. The expandable balloon 20 may be a separate component from the outer sleeve 16 coupled thereto by conventional methodologies. In one embodiment, the expandable balloon 20 is monolithically formed with the outer sleeve 16 from, e.g., a suitable elastomeric material. For example, the expandable balloon 20 may be a balloon segment of the outer sleeve 16, which is subjected to a molding or thermoforming process to be capable of transitioning between unexpanded and at least partially expanded conditions. The expandable balloon 20 expands radially outwardly upon passage of inflation fluids through the fluid port 38, the conduits 36 and within an internal volume 20v of the expandable balloon 20.

The expandable balloon 20 is mounted about the annular recess 32 in the cannula member 14. In embodiments, the annular recess 32 creates a void or space to receive the inflation fluids distributed through the conduits 36 thereby facilitating entry of the inflation fluids within the internal volume 20v of the expandable balloon 20. In addition, the expandable balloon 20, when in its unexpanded condition, may be at least partially received within the annular recess 32 during insertion of the cannula member 14 relative to tissue thereby reducing the overall profile of the cannula member 14. The proximal end of the expandable balloon 20 may be secured to a segment of the cannula member 14 proximal of the annular recess 32 and the distal end of the expandable balloon 20 may be secured to the cannula tip 34. The intermediate portion of the expandable balloon 20 is unattached. Securement of the expandable balloon 20 may be effected through any of the aforementioned methodologies discussed hereinabove in connection with the outer sleeve 16. In other embodiments, the expandable balloon 20 may be secured relative to the cannula member 14 through an interference or friction fit.

Figure 8:
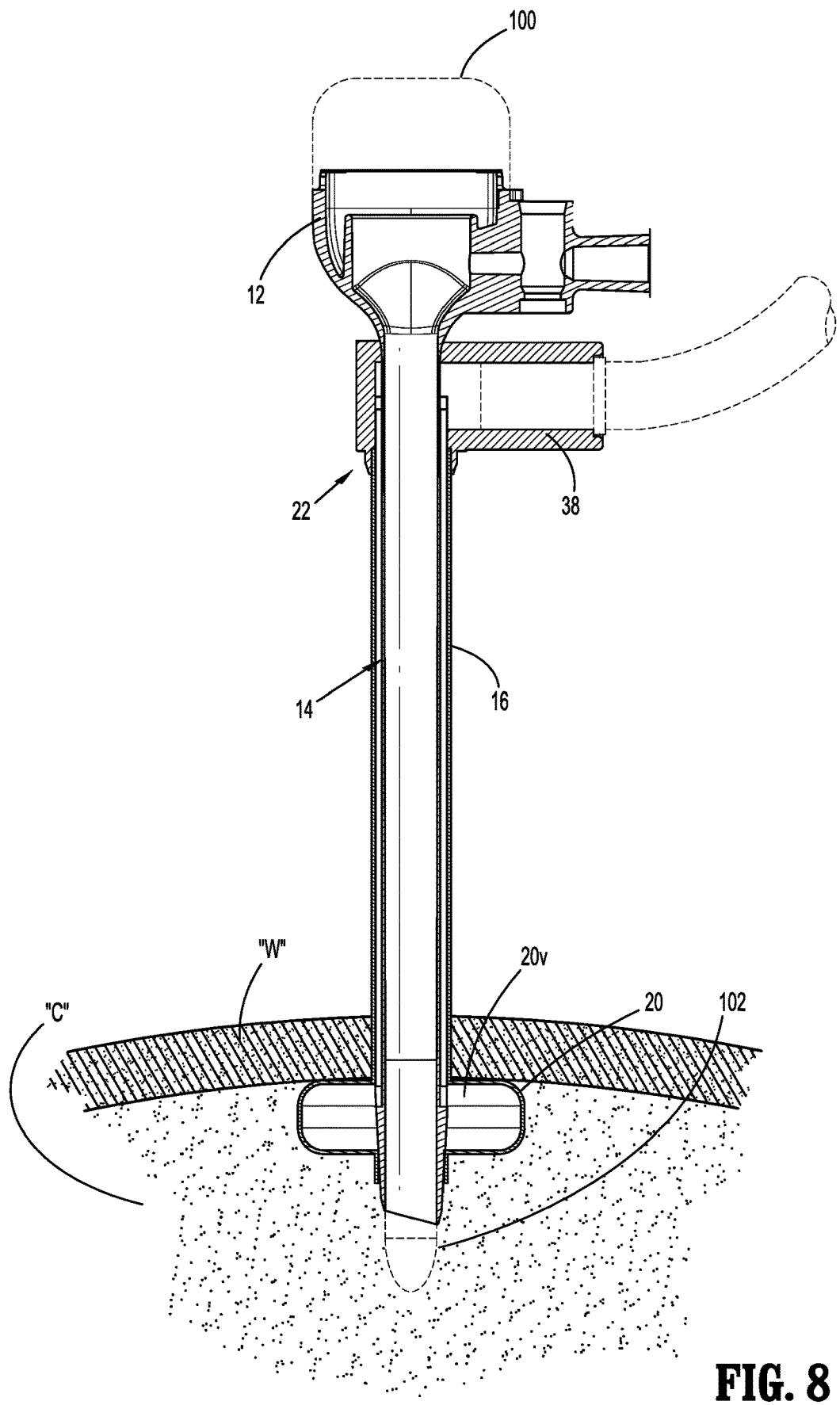
FIG. 8 is a view illustrating positioning of the cannula assembly within a body cavity with the expandable balloon in an expanded condition thereof.
Figures 9, 10:
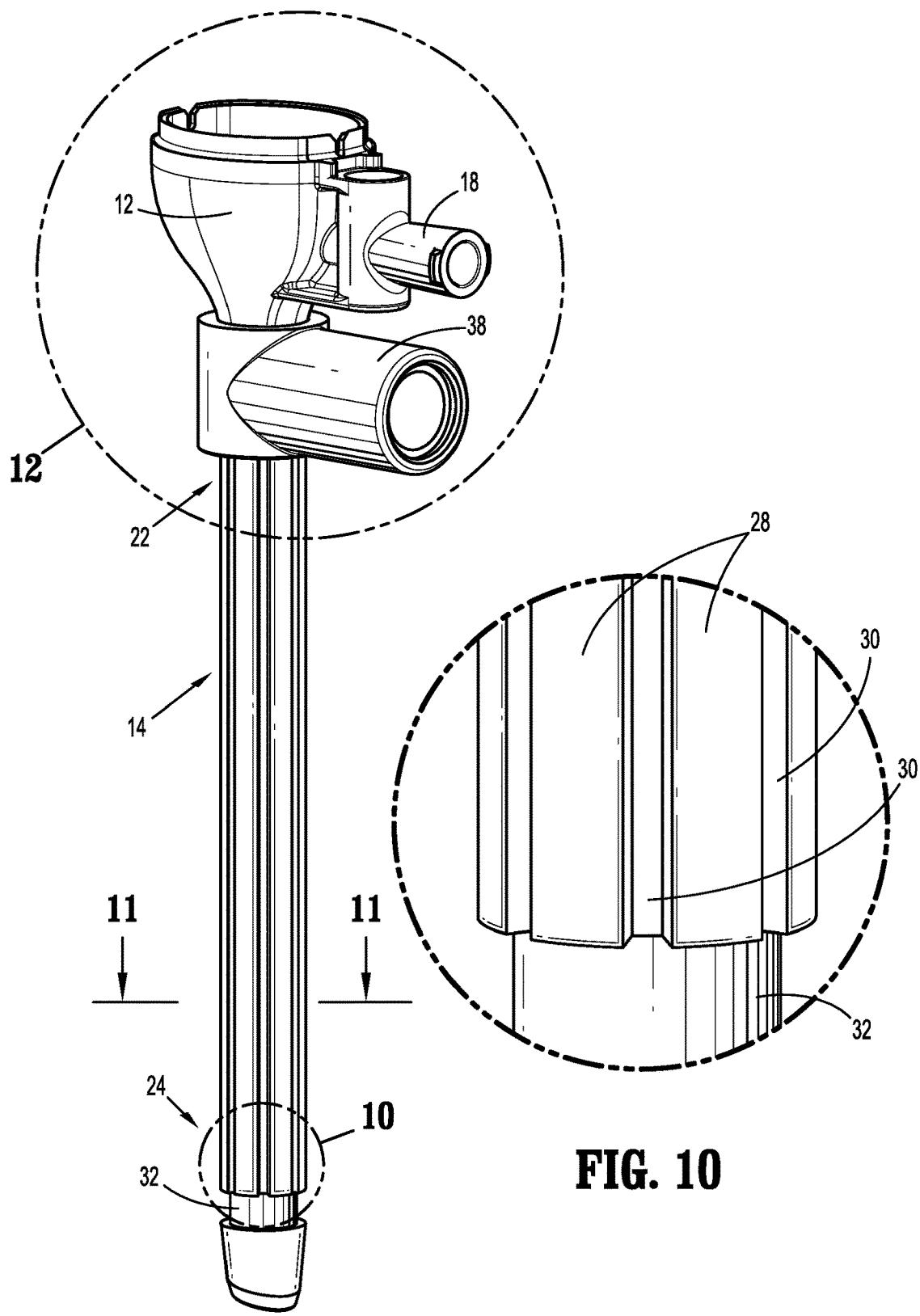
FIG. 9 is a perspective view of another exemplary embodiment of the cannula assembly where the conduits are removed from the longitudinal channels.
FIG. 10 is an enlarged view of the area of detail depicted in FIG. 9.
Figure 11:
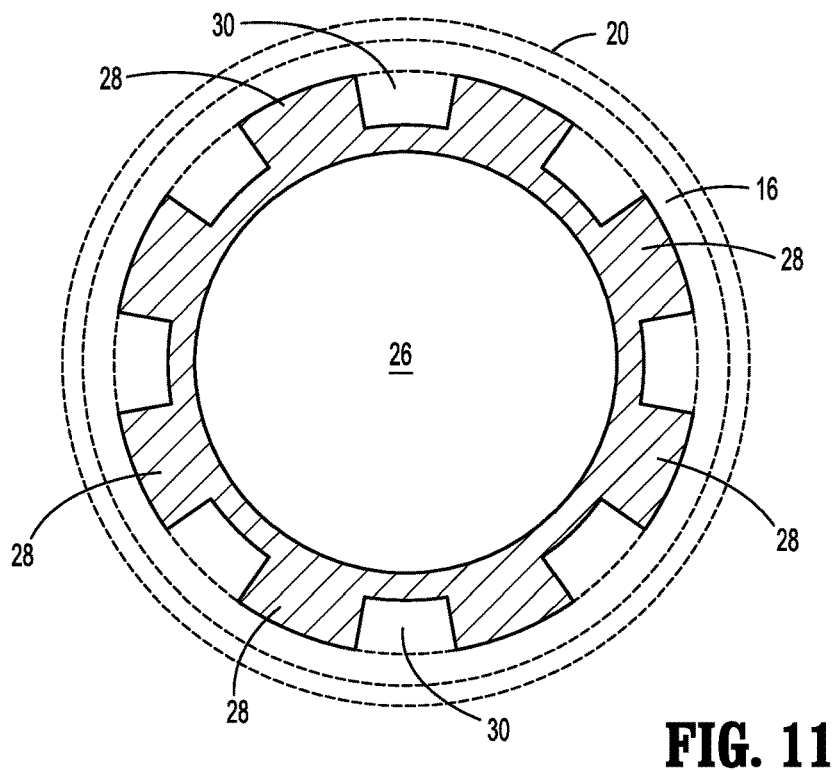
FIG. 11 is a cross-sectional view taken along the lines 11-11 of FIG. 9.
Figure 12:
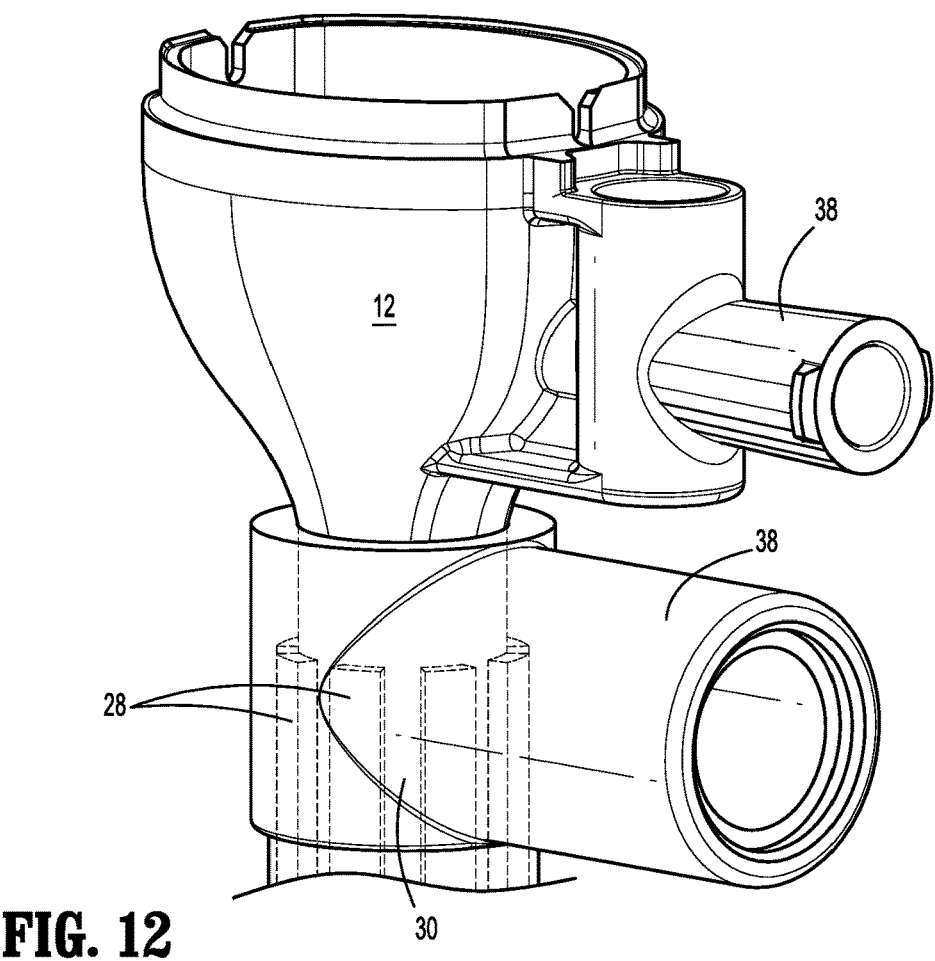
FIG. 12 is an enlarged view of the area of detail depicted in FIG. 9.

FIG. 8 illustrates the cannula assembly 10 accessing an underlying cavity, e.g., the abdominal cavity "c". In one methodology, the abdominal cavity "c" is insufflated to establish a pneumoperitoneum. The obturator 100 is positioned within the cannula assembly 10 and the assembled unit is advanced to penetrate the abdominal wall "w". Inflation fluids are introduced through the fluid port 38 and communicate through the conduits 36 into the internal volume 20v of the expandable balloon 20. In the expanded or at least partially expanded condition depicted in FIG. 8, the expandable balloon 20 will resist withdrawal of the cannula assembly 10 from the abdominal cavity "c" while also providing a seal within the internal surface of the abdominal wall "w" minimizing passage of fluids, including inflation fluids, from the abdominal cavity "c". A cuff of fixation locking collar (not shown) may be positioned about the proximal end 22 of the cannula assembly 10 and advanced to engage the exterior surface of the abdominal wall "w". The cuff in combination with the expandable balloon 20 will minimize movement of the cannula member 14 in both withdrawal and insertion directions and also assist in maintaining a seal about the passage in the abdominal wall "w".

FIGS. 9-12 illustrate one embodiment where the conduits 36 are removed leaving the longitudinal channels 30 within the cannula member 14 as the path(s) to communicate the inflation fluids to the expandable balloon 20. In accordance with this embodiment, the longitudinal channels 30 are enclosed along their respective lengths by the outer sleeve 16 which is fabricated from an elastomeric material and establishes a seal about the cannula member 14. This arrangement may permit a greater flow rate of inflation fluids to the expandable balloon 20 due to the greater volume or cross-sectional areas of the longitudinal channels 30 compared to the cross-sectional areas of the conduits 36. The longitudinal ribs 28 are spaced to minimize the potential of collapsing of the outer sleeve 16 within one or more longitudinal channels 30. The multiple longitudinal channels 30 will ensure passage of inflations fluids even in the event one or more longitudinal channels 30 are obstructed.

In another embodiment, the cannula member 14 may include one or more conduits 36 within the longitudinal channels 30 and one or more longitudinal channels 30 devoid of conduits 36. With this embodiment, both the conduits 36 and the unoccupied longitudinal channels 30 define flow paths along which the inflation fluids pass to the internal volume 20v of the expandable balloon 20.

Figure 13:
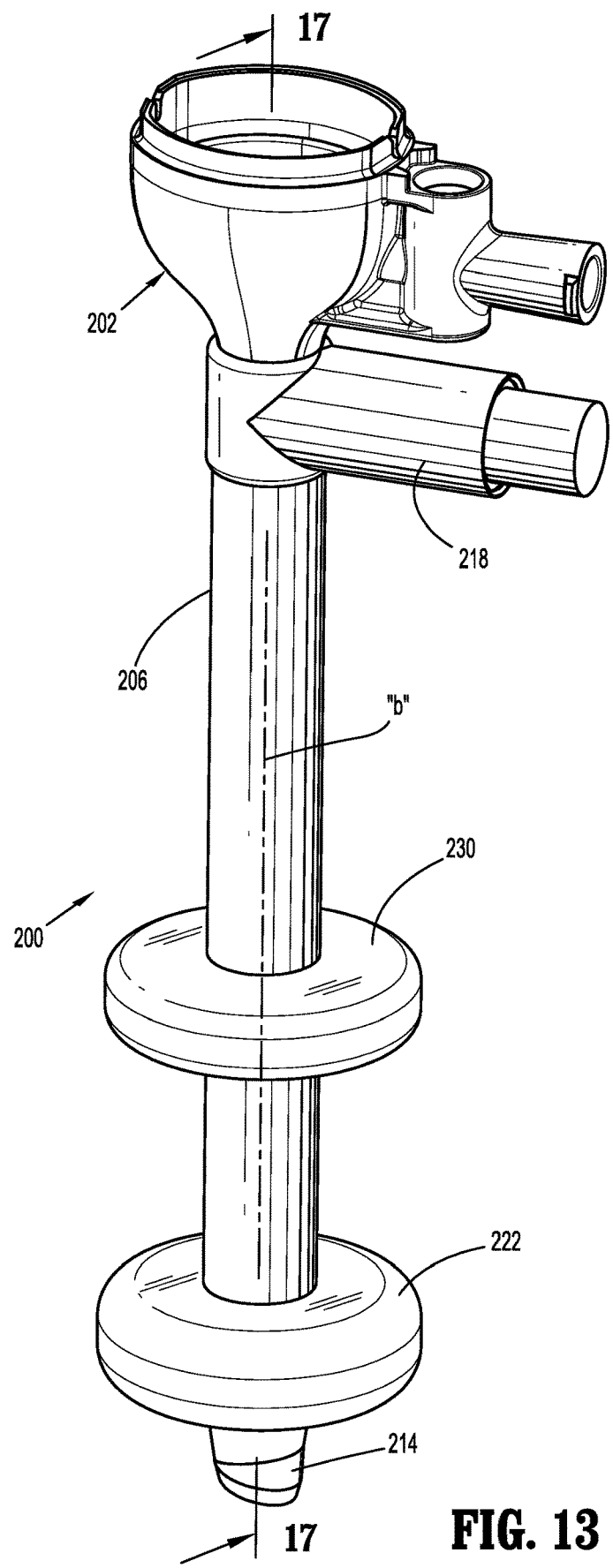
FIG. 13 is a perspective view of another exemplary embodiment of the cannula assembly illustrating a single longitudinal groove with a single conduit leading to a balloon segment.
Figure 14:
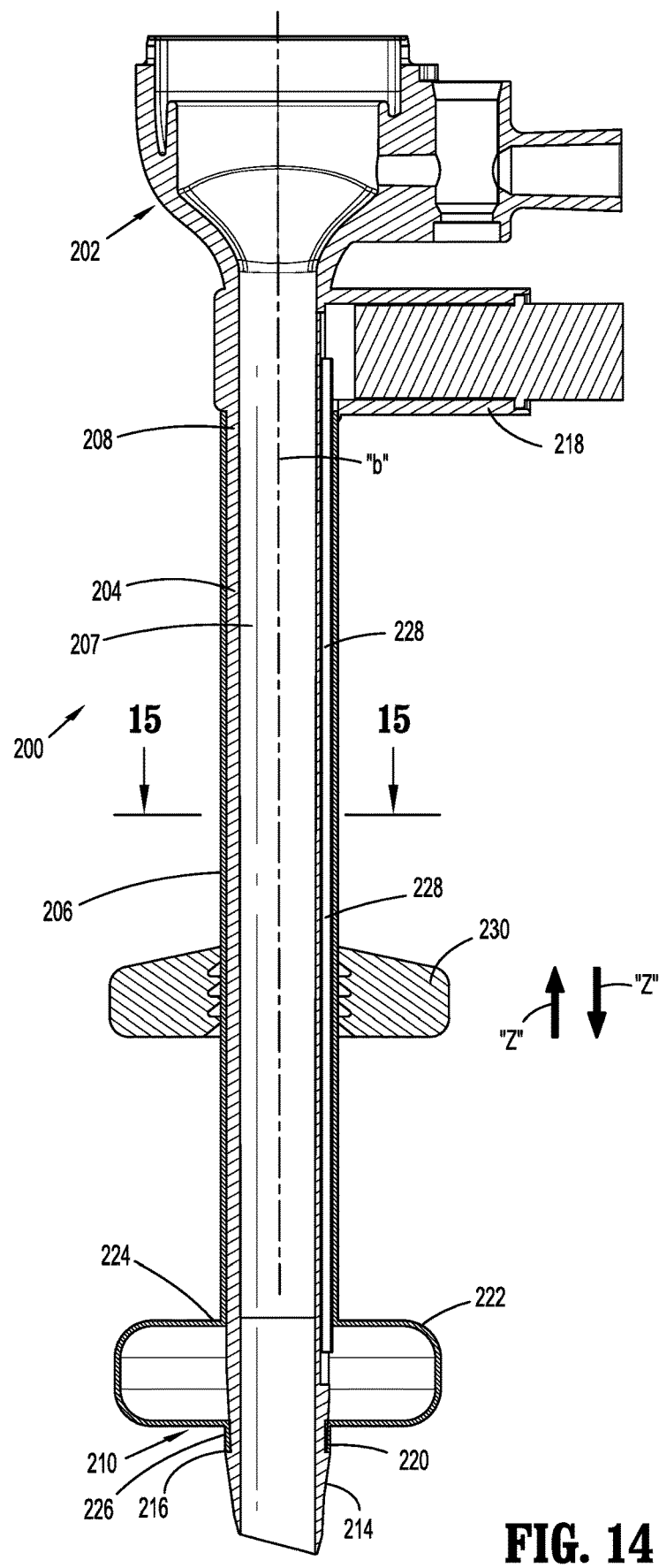
FIG. 14 is a side cross-sectional view of the cannula assembly of FIG. 13.
Figure 15:
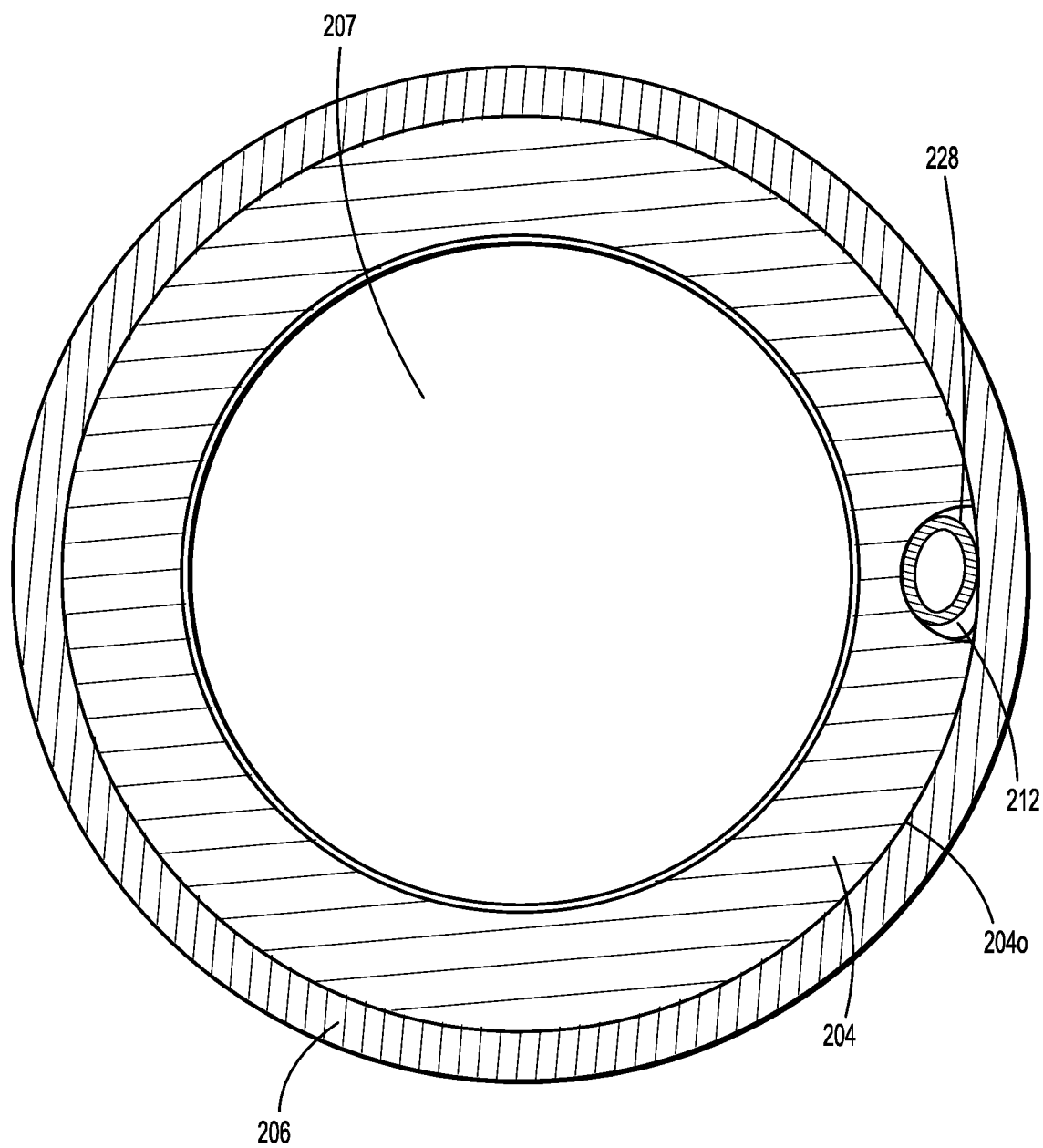
FIG. 15 is a cross-sectional view taken along the lines 15-15 of FIG. 14.

Referring now to FIGS. 13-15, another exemplary embodiment of the cannula assembly of the present disclosure is illustrated. The cannula assembly 200 includes a cannula housing 202, a cannula member 204 extending from the cannula housing 202 and defining a longitudinal axis "b" and an outer sleeve 206 which is coaxially mounted about the cannula member 204. The cannula housing 202 is substantially similar to the cannula housing 12 of the embodiment of FIGS. 1-8. The cannula member 204 defines a longitudinal lumen 207 and proximal and distal ends 208, 210. The cannula member 204 has a single longitudinal groove 212 defined in its outer surface 204o and extending along the longitudinal axis "b" for a majority of the length of the cannula member 204. In embodiments, the single longitudinal groove 212 is linear and parallel to the longitudinal axis "b", and may extend through the proximal end 208 of the cannula member 204. In the alternative, the single longitudinal groove 212 may have one or more curves or possess segments which are offset with respect to the longitudinal axis "b". The single longitudinal groove 212 may have a U-shaped or rounded cross-section as shown. The cannula member 204 has a cannula tip 214 adjacent its distal end 210. The cannula tip 214 defines a stepped region or ledge 216 which facilitates securement of the outer sleeve 206 as will be discussed.

The outer sleeve 206 extends along the cannula member 204 and is fluidly coupled, at its proximal end, to the fluid port 218 of the cannula housing 202. The outer sleeve 206 may be secured relative to the fluid port 218 through any of the aforementioned methodologies. The distal end 220 of the outer sleeve 206 is secured to the cannula member 204 adjacent the stepped region or ledge 216. In embodiments, the ledge 216 defines a maximum outer dimension which is substantially equivalent to the outer dimension of the outer sleeve 206 to provide a smooth transition between the cannula tip 214 and the outer sleeve 206.

In embodiments, the outer sleeve 206 is monolithically formed incorporating a balloon segment 222 adjacent its distal end 220. The balloon segment 222 is capable of transitioning between an unexpanded condition and an expanded condition (FIG. 13). In the unexpanded condition, the balloon segment 222 may be substantially flush with the outer surface 204o of the cannula member 204. The balloon segment 222 may define proximal and distal ends 224, 226. The proximal end 224 may or may not be secured to the cannula member 204. The distal end 226 of the balloon segment 222 may coincide with the distal end 220 of the outer sleeve 206 and may be secured adjacent the ledge 216 as discussed hereinabove.

A single conduit or tube 228 is disposed within the single longitudinal groove 212 of the cannula member 204 and extends from within the fluid port 218 at one end and terminates within the balloon segment 222 at its other end. The conduit 228 may be fabricated from a polyurethane or other relatively soft elastomeric material. The conduit 228 may define a substantially circular cross-sectional dimension when in an unstressed condition thereof. In embodiments, the outer dimension of the conduit 228 is greater than the radial depth of the single longitudinal groove 212. Thus, upon assembly of the outer sleeve 206 about the cannula member 204, the conduit 228 may be compressed by the outer sleeve 206 to assume the oval configuration confined, and optionally secured, within the single longitudinal groove 212 as shown in FIG. 15. In the alternative, the single longitudinal groove 212 may include multiple conduits 228 at least partially disposed therein.

The cannula assembly 200 may further include a collar 230 mounted about the cannula member 204. The collar 230 may be fabricated from foam or the like and is adapted for reciprocal longitudinal movement along the cannula member 204 in the direction of directional arrows "z" for positioning against the abdominal wall to facilitate securing of the cannula member 204 relative to the abdominal wall.

The cannula assembly 200 is utilized in a surgical procedure in a similar manner to the embodiments of FIGS. 1-12. The single longitudinal groove 212 and associated single conduit 228 may be dimensioned to provide a predetermined flow rate facilitating uniform expansion and deflation of the balloon segment 222. The single conduit 228 also may reduce the rate of deflation of the balloon segment 222 to minimize the potential of vacuum forces being created within the balloon segment 222 and/or the single conduit 228 to avoid collapse of these components during deflation.

Figure 16:
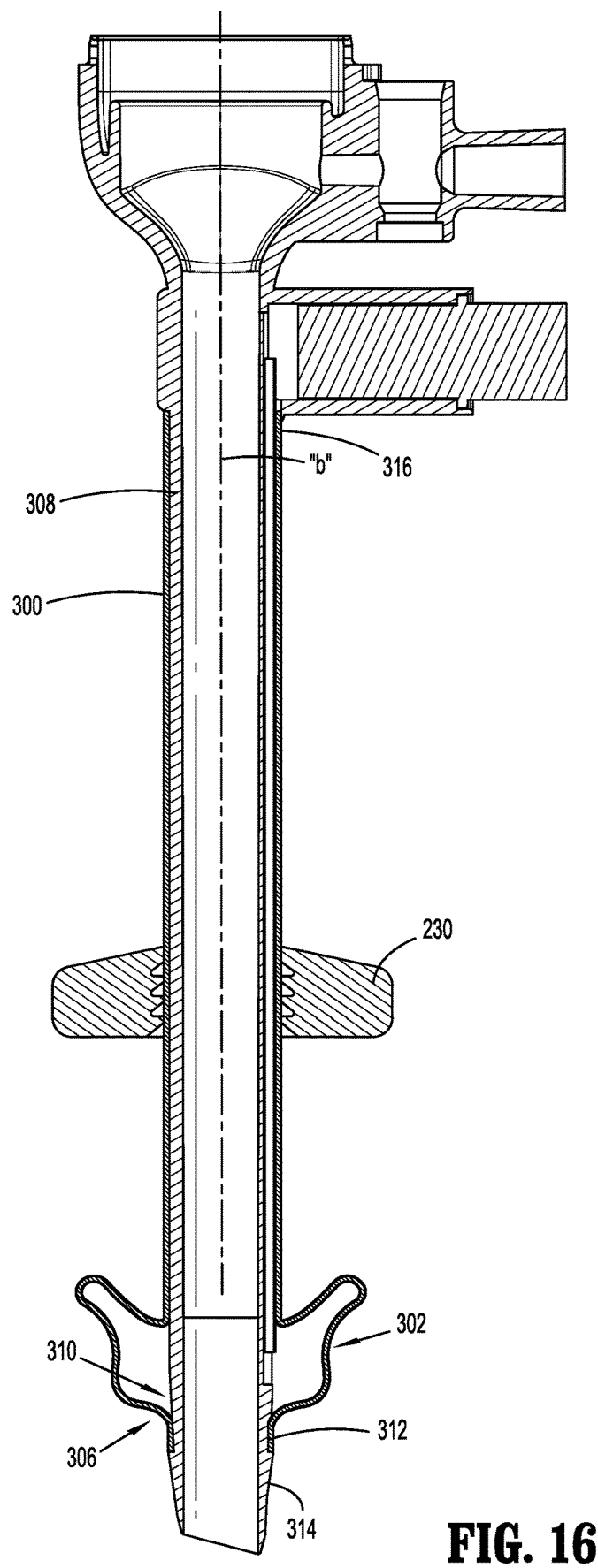
FIG. 16 is a side cross-sectional view of another exemplary embodiment of the cannula assembly illustrating an inverted balloon segment when in an unexpanded condition thereof.
Figure 17:
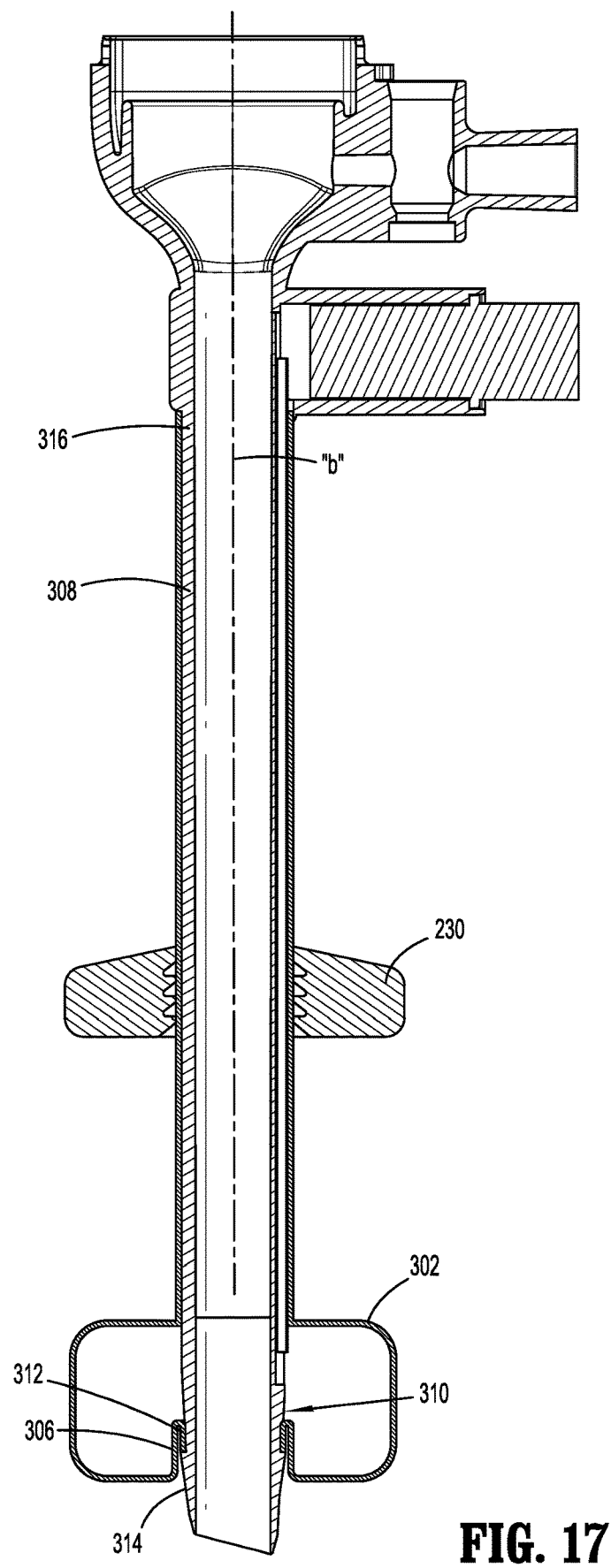
FIG. 17 is a side cross-sectional view of the cannula assembly of FIG. 15 with the balloon segment in an expanded condition.

Referring now to FIGS. 16-17, another exemplary embodiment of the cannula assembly of the present disclosure is illustrated. This cannula assembly 300 is similar to the cannula assembly 200 of the embodiment of FIGS. 13-15. However, in accordance with this embodiment, the outer sleeve 300 defines an inverted balloon segment 302 in the unexpanded condition of the balloon segment 302. The outer sleeve 302 may be thermoformed or molded during manufacture to create the balloon segment 302 with the inverted shape. In embodiments, the distal end 306 of the outer sleeve 302 is attached to the cannula 308 only along a small area or length of the distal end 310 of the cannula 308. For example, the area of attachment 312 of the distal end 306 of the outer sleeve 302 to the distal end 310 of the cannula 308 may be reduced by at least fifty (50) % in length compared to the prior embodiments (see, e.g., FIG. 14). This creates additional slack in the unexpanded balloon segment 302, and in conjunction with the elasticity of the outer sleeve 300, permits the balloon segment 302 to assume its inverted condition when unexpanded. In addition, or alternatively, the area of attachment 312 of the distal end 306 of the outer sleeve 302 may be more proximal relative to prior embodiments thereby creating even more additional slack in the outer sleeve 300. The outer sleeve 300 adjacent the proximal end of the balloon segment 302 may be secured to the cannula 308 similar to prior embodiments.

FIG. 17 illustrates the balloon segment 302 in the expanded condition. Due at least in part to the inverted arrangement of the balloon segment 302, upon expansion to the expanded condition, the balloon segment 302 extends at least partially beyond the area of attachment 312 of the distal end 306 of the outer sleeve 300 to the cannula 308 such that the distal end 306 of the outer sleeve 300 is at least partially confined within the balloon segment 302. More significantly, the balloon segment 302 extends further relative to, or along, the penetrating tip 314 of the cannula 306 (e.g., beyond the area of attachment 312 of the outer sleeve 302) such that only a small portion of the penetrating tip 314 is exposed beyond the balloon segment 302. Thus, when positioned within the abdominal cavity and with the balloon segment 302 in the expanded condition, only a relatively small portion or length of the penetrating tip 314 extends within the abdominal cavity. Since there is less of the penetrating tip 314 within the abdominal cavity, visualization with, e.g., an endoscope or laparoscope introduced through the cannula 306 and within the abdominal cavity is enhanced.

In other regards, the cannula assembly 300 is similar in configuration and use to the cannula assembly 200 of the embodiment of FIGS. 13-15. The proximal end 316 of the outer sleeve 300 may or may not be attached to the proximal end of the cannula 306. The beveled penetrating tip 314 of the cannula 306 is utilized to facilitate passage through the abdominal wall when in the unexpanded condition of the balloon segment 302.

Due at least in part to the inverted arrangement of the balloon segment 302, upon expansion to the expanded condition, the balloon segment 302 extends at least partially beyond the area of attachment 312 of the distal end 306 of the outer sleeve 300 to the cannula 308 such that the distal end 306 of the outer sleeve 300 is at least partially confined within the balloon segment 302. More significantly, the balloon segment 302 extends further relative to, or along, the penetrating tip 314 of the cannula 306 (e.g., beyond the area of attachment 312 of the outer sleeve 302) such that only a small portion of the penetrating tip 314 is exposed beyond the balloon segment 302. Thus, when positioned within the abdominal cavity and with the balloon segment 302 in the expanded condition, only a relatively small portion or length of the penetrating tip 314 extends within the abdominal cavity. Since there is less of the penetrating tip 314 within the abdominal cavity, visualization with, e.g., an endoscope or laparoscope introduced through the cannula 306 and within the abdominal cavity is enhanced.

In other regards, the cannula assembly 300 is similar in configuration and use to the cannula assembly 200 of the embodiment of FIGS. 13-15. The proximal end 316 of the outer sleeve 300 may or may not be attached to the proximal end of the cannula 306. The beveled penetrating tip 314 of the cannula 306 is utilized to facilitate passage through the abdominal wall when in the unexpanded condition of the balloon segment 302.

Figure 18:
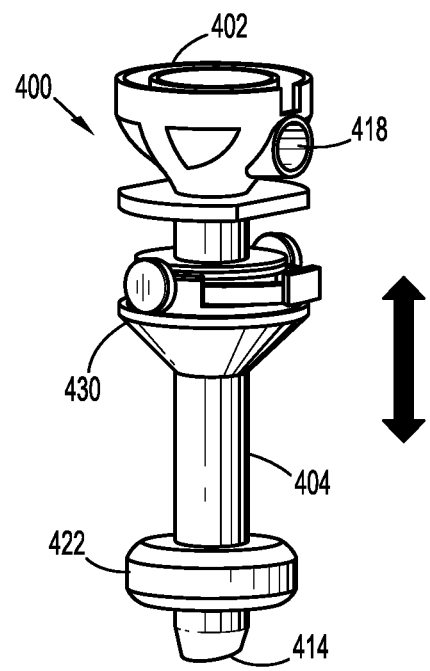
FIG. 18 is a perspective view of a cannula assembly in another example according to the present disclosure.

In a further example of an access assembly, a cannula assembly 400, which can be used with any bladed, bladeless and/or optical obturator, is shown in FIG. 18. The cannula assembly has a cannula housing 402 for housing one or more seals (instrument seal, zero closure seal, duckbill seal, etc.), a distal tip 414, an insufflation port 418, and an expandable member 422 similar to those disclosed above. In this example, the fixation member is replaced with a fixation collar assembly 430. The fixation collar assembly is movable along the cannula member 404 and has a lock member 403.

The fixation collar assembly 430 has the aforementioned lock member 403, in addition to a plug 401 that is conical in shape. The lock member has a large tab 405 and a small tab 406 for locking and unlocking the position of the fixation collar assembly 430. The assembly has a plug support 422 for supporting the plug 401 and the lock member 403. The plug support 422 defines one or more suture fixation members 423 which can be formed as bumps. In the example shown, the suture fixation bumps are circular features at diametrically opposed locations on the plug support 422. The plug 401 has a plug neck 444 that is an upward extension of the plug 401 material and cylindrical in shape. The plug neck 444 may have features 447 on an inner surface 446 thereof for assisting in frictional engagement with the outer surface of the cannula member. For example, ridges or bumps 447 are defined on the inner surface 446.

Figure 19:
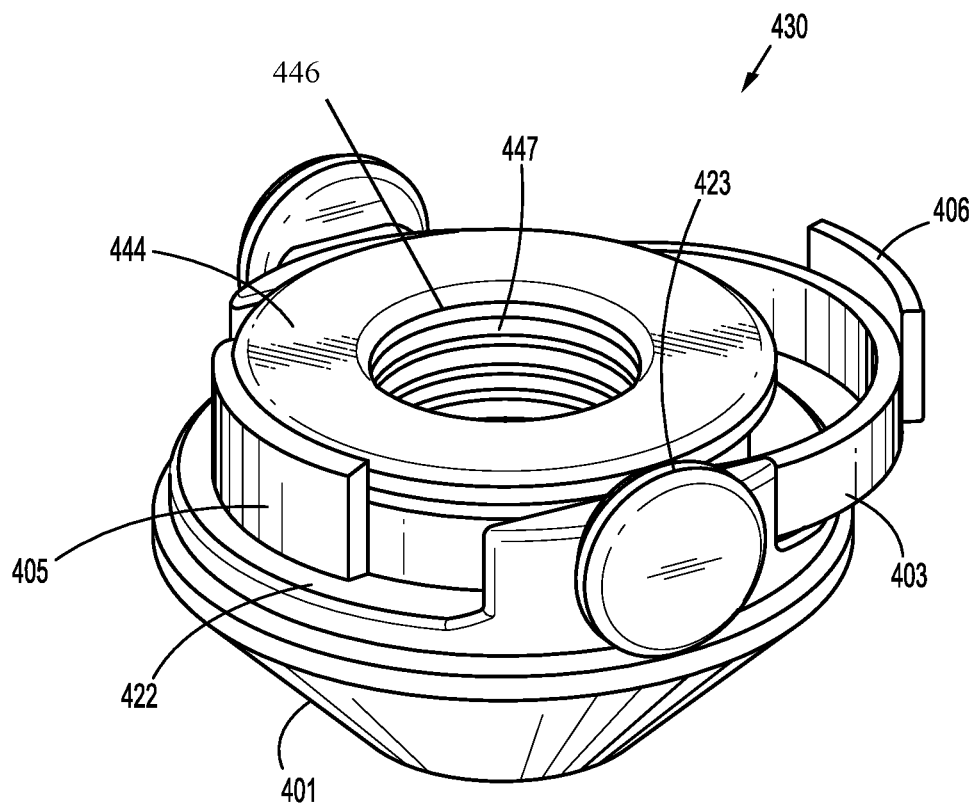
FIG. 19 is a perspective view of a fixation collar assembly.
Figure 20:
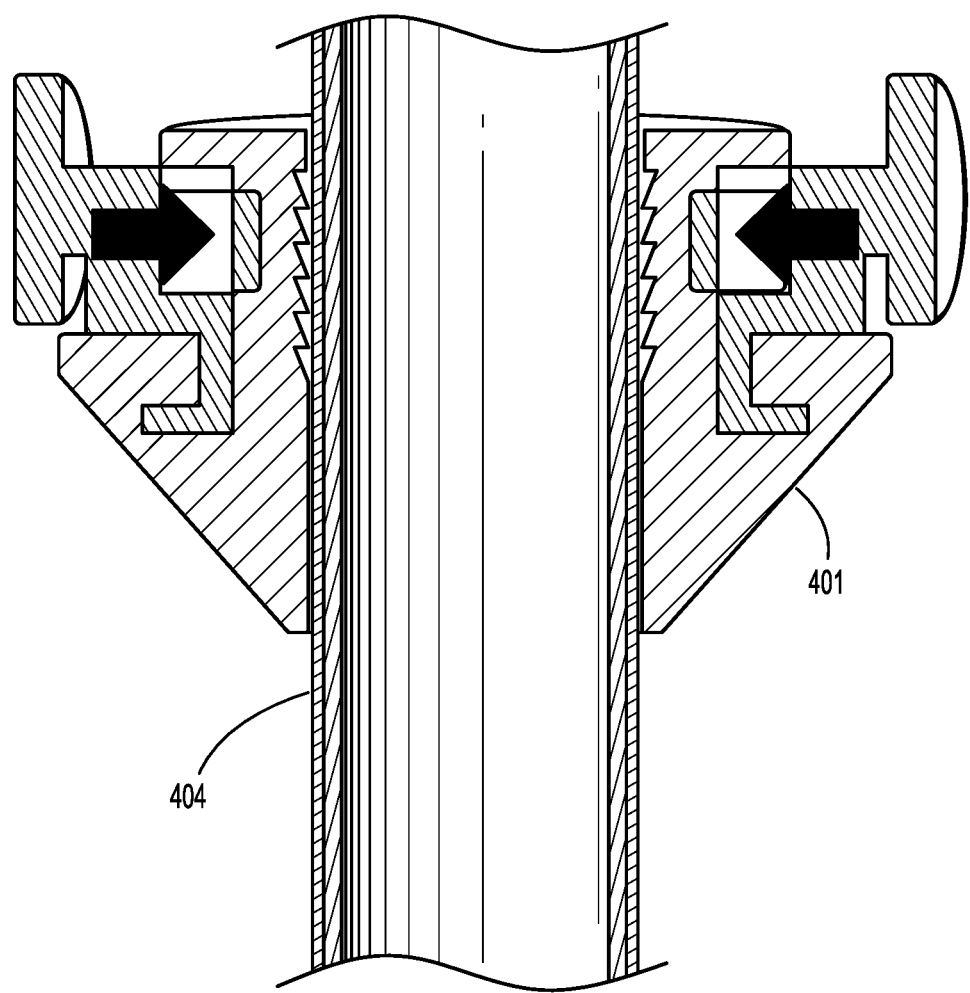
FIG. 20 is an area of detail from FIG. 18 showing a fixation collar assembly.

The lock member 403 is supported on the plug 401, surrounding the plug neck 444 and has a large tab 405 for locking the position of the fixation collar assembly, and a small tab 406 for unlocking the position of the fixation collar assembly. The large tab and small tab are positioned at diametrically opposed locations on the lock member 403, surrounding the neck 444. (see FIG. 19).

Figure 22:
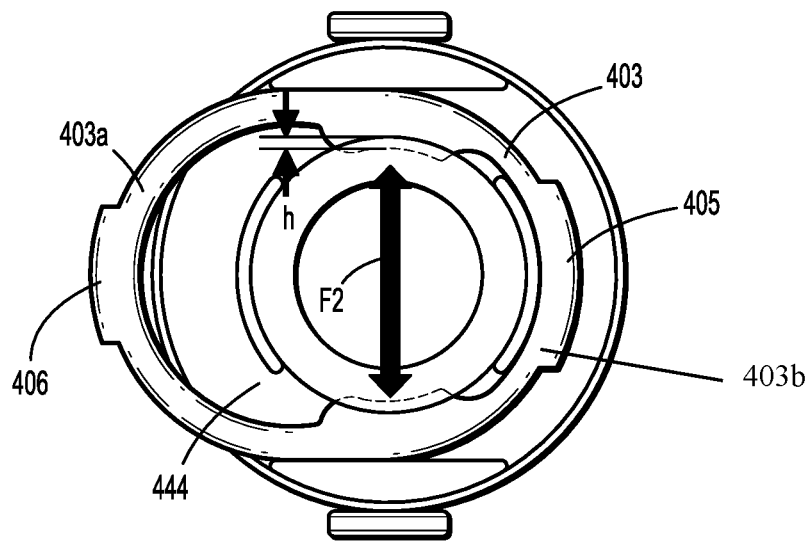
FIG. 22 is another plan view the fixation collar assembly shown in FIGS. 18-21.

When the large tab 405 is pressed, the neck 444 of the plug 401 is compressed and the neck 444 is transitioned from a loose interference with the outer surface of the cannula member to a forced interference therewith, by compressing the neck 444 of the plug 401 against the surface of the cannula member 404. The view of FIG. 22 shows the lock member 403 compressing the neck 444 of the plug 401 against the cannula member. A first end of the lock member has a different dimension than the second end of the lock member (the difference is shown as "h"). The lower end of the plug 401 defines a conical shape for gentle engagement with the incision in the abdomen. The plug 401 can be formed from a polyurethane foam, molded elastomeric material such as Krayton, Santoprene, or silicone.

Figure 21:
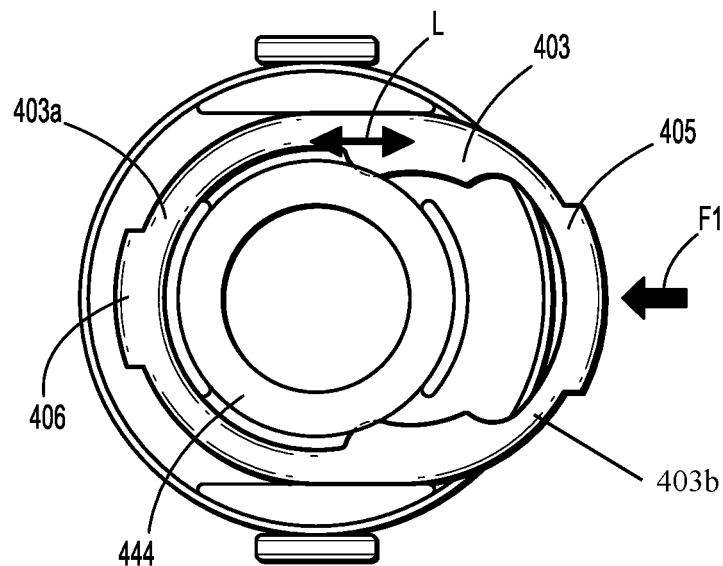
FIG. 21 is a plan view of the fixation collar assembly shown in FIGS. 18-20.

FIGS. 21 and 22 show a top view of the lock member 403. The lock member is oblong in shape and defines an interior surface. An end 403a of the lock member adjacent the small tab 406 has an interior volume that is relatively large compared to the size of the neck 444 of the plug 401, whereas an end 403b of the lock member adjacent the large tab 405 has an interior volume that is relatively small compared to the size of the neck 444. Thus, by sliding the lock member 403 laterally with respect to the neck 444, the end of the lock member 403 with the smaller volume can be engaged with the neck member, compressing it against the cannula member.

It is contemplated that the lock member can have other configurations. It could be a clip of another arrangement, having one or more moving parts. It could be configured as a latch.

The compliant or resilient material of the plug 401 having a low Young's modulus reduces the compression force variation, and the size and shape of the lock member can be varied to work with different materials for the plug 401.

The fixation collar assembly 430 has many benefits. It prevents injury to abdominal organs by minimizing unintentional trocar displacement. It provides cannula fixation and articulation while minimizing the fascial defect. Pneumoperitoneum is maintained and convenient one-hand operation is provided. Procedure time is reduced because the access assembly is easy to use and prevents pulling in of the trocar. The working length is minimized by minimizing the fixation collar assembly height. It has the combination of a wide conical plug made of compliant materials and compact low profile lock member, minimizing potential trauma to the patient's skin. Reliability is improved.

While the invention has been particularly shown and described with reference to the preferred embodiments, it will be understood by those skilled in the art that various modifications and changes in form and detail may be made therein without departing from the scope and spirit of the invention. Accordingly, the above description should not be construed as limiting, but merely as exemplifications of preferred embodiments. Thus, modifications such as those suggested above, but not limited thereto, are to be considered within the scope of the invention.

What is claimed is:
1. A surgical cannula assembly, comprising:
an elongate cannula member defining a longitudinal axis and having proximal and distal ends, the cannula member including a plurality of longitudinal ribs extending along the longitudinal axis, the plurality of longitudinal ribs positioned about the elongate cannula member so that the elongate cannula member has at least two degrees of rotational symmetry wherein each plane of a plurality of transverse planes intersecting one another across a diameter of the elongate cannula member separates symmetrical halves of the elongate cannula member, adjacent longitudinal ribs of the plurality of longitudinal ribs defining separate and discrete longitudinal channels therebetween that open distally into an annular recess disposed in fluid communication with each of the separate and discrete longitudinal channels;
a fluid port mounted adjacent the proximal end of the cannula member, the fluid port configured for coupling to a source of inflation fluids;
a conduit positioned within at least one longitudinal channel of the longitudinal channels of the cannula member, the conduit in fluid communication with the fluid port; and
an expandable balloon mounted adjacent the distal end of the cannula member and in fluid communication with the conduit, the expandable balloon configured to transition from an initial unexpanded condition to an at least partially expanded condition upon passage and entry of inflation fluids through the conduit and within an internal volume of the expandable balloon.

2. The surgical cannula assembly according to claim 1 including an outer sleeve coaxially mounted about the cannula member, the outer sleeve coupled to the expandable balloon.

3. The surgical cannula assembly according to claim 2 wherein the outer sleeve and the expandable balloon are monolithically formed.

4. The surgical cannula assembly according to claim 3 wherein the outer sleeve and the expandable balloon comprise an elastomeric material.

5. The cannula assembly according to claim 1 wherein the conduit includes a plurality of conduits, each conduit positioned within a respective longitudinal channel of the longitudinal channels defined by the adjacent longitudinal ribs, each conduit in fluid communication with the fluid port and the internal volume of the expandable balloon.

6. The surgical cannula assembly according to claim 1 including a cannula housing mounted adjacent the proximal end of the cannula member, the cannula housing including an inflation connector, the inflation connector in fluid communication with a longitudinal lumen defined within the cannula member.

7. The surgical cannula assembly of claim 1, wherein the plurality of longitudinal ribs and longitudinal channels are obliquely arranged relative to the longitudinal axis.

8. A surgical cannula assembly, comprising:
a cannula housing;
a cannula member defining a longitudinal axis, and a longitudinal lumen configured to permit passage of a surgical object, the cannula member having a plurality of longitudinal ribs on an outer surface thereof with each rib of the plurality of longitudinal ribs having substantially the same width, the plurality of longitudinal ribs extending completely around a circumference of the outer surface, adjacent longitudinal ribs of the plurality of longitudinal ribs defining separate and discrete longitudinal channels therebetween that open distally into an annular recess disposed in fluid communication with each of the separate and discrete longitudinal channels;
a conduit at least partially positioned within one longitudinal channel of the longitudinal channels of the cannula member;
a fluid port in fluid communication with the conduit and configured for coupling to a source of inflation fluids; and
an outer sleeve coaxially mounted about the cannula member, the outer sleeve having an expandable balloon in fluid communication with the conduit, the expandable balloon configured to transition from an initial unexpanded condition to an at least partially expanded condition upon passage of inflation fluids from the fluid port, through the conduit and within an internal volume of the expandable balloon.

9. The surgical cannula assembly according to claim 8 including a second conduit at least partially positioned within a second longitudinal channel of the longitudinal channels of the cannula member, the second conduit being in fluid communication with the fluid port and with the internal volume of the expandable balloon.

10. The surgical cannula assembly according to claim 8 wherein the cannula member includes a second longitudinal channel of the longitudinal channels defined between the adjacent longitudinal ribs, the second longitudinal channel in fluid communication with the fluid port and with the internal volume of the expandable balloon.

11. A surgical cannula assembly, comprising:
a cannula housing;
a cannula member defining a longitudinal axis, and a longitudinal lumen configured to permit passage of a surgical object, the cannula member having an outer surface that defines a circumference, the circumference being a sum of a first arc and a second arc, the first arc having a first radius extending from a first center point, the second arc having a second radius extending from a second center point that is different from the first center point, the second arc defining a single longitudinal groove in the outer surface of the cannula member;
a fixation collar assembly supported on the cannula member and including a lock member that has a fixed profile, the lock member positioned to slide in a direction transverse to the longitudinal axis of the cannula member and relative to the fixation collar assembly to selectively secure the position of the fixation collar assembly relative to the cannula member;
a conduit at least partially positioned within the single longitudinal groove of the cannula member;
a fluid port in fluid communication with the conduit and configured for coupling to a source of inflation fluids; and
an outer sleeve coaxially mounted about the cannula member and positioned to compress the conduit within the longitudinal groove, the outer sleeve having an expandable balloon segment in fluid communication with the conduit, the expandable balloon segment configured to transition from an initial unexpanded condition to an at least partially expanded condition upon passage of inflation fluids from the fluid port, through the conduit and within an internal volume of the expandable balloon segment.

12. The surgical cannula assembly according to claim 11 wherein the outer sleeve is configured to extend along a majority of a longitudinal length of the cannula member.

13. The surgical cannula assembly according to claim 12 wherein the outer sleeve is secured to the cannula member adjacent proximal and distal balloon ends of the balloon segment.

14. The surgical cannula assembly according to claim 12 wherein the outer sleeve comprises an elastomeric material.

15. The surgical cannula assembly according to claim 14 wherein the balloon segment is configured to assume an at least partially inverted condition when in the unexpanded condition thereof.

16. The surgical cannula assembly according to claim 14 wherein the outer sleeve is secured to the cannula member at an area of attachment, the balloon segment being configured to extend distally beyond the area of attachment when in an at least partially expanded condition.

17. The surgical cannula assembly according to claim 12, wherein the fixation collar assembly is disposed on the cannula member proximal to the expandable balloon segment and is slidably engaged with the outer surface of the cannula member, the fixation collar assembly having a compliant or resilient plug with a conically shaped lower end and an upper end, the lock member is laterally movable and has an interior volume shaped for transitioning the upper end from a relatively uncompressed state to a compressed state.

18. The surgical cannula assembly according to claim 11 wherein the single longitudinal groove is in parallel relation to the longitudinal axis of the cannula member.

19. The surgical cannula assembly of claim 11, wherein the lock member is oblong and has an interior surface defining an irregular shaped opening therethrough, the lock member positioned to slide in a first direction transverse to the longitudinal axis of the cannula member to cause the irregular shaped opening secure the position of the fixation collar assembly relative to the cannula member and to slide in a second direction opposite to the first direction to enable the fixation collar assembly to move relative to the cannula member.

* * * * *